United States Patent [19]

Rüger et al.

[11] Patent Number: 4,999,370

[45] Date of Patent: Mar. 12, 1991

[54] COMPOUNDS WITH A PSYCHOTROPIC ACTION, AGENTS CONTAINING THEM, AND THE USE THEREOF FOR THE TREATMENT AND PROPHYLAXIS OF DISORDERS OF THE CENTRAL NERVOUS SYSTEM

[75] Inventors: Wolfgang Rüger, Kelkheim; Hansjörg Urbach, Kronberg/Taunus; Rainer Henning, Hattersheim am Main; Jens Stechl, Frankfurt am Main; Patricia Usinger, Eppstein/Taunus; Franz Hock, Dieburg, all of Fed. Rep. of Germany

[73] Assignee: Hoechst Aktiengesellschaft, Frankfurt am Main, Fed. Rep. of Germany

[21] Appl. No.: 301,297

[22] Filed: Jan. 25, 1989

[30] Foreign Application Priority Data

Jan. 27, 1988 [DE] Fed. Rep. of Germany ....... 3802303
Jan. 30, 1988 [DE] Fed. Rep. of Germany ....... 3802760
Apr. 22, 1988 [DE] Fed. Rep. of Germany ....... 3813819

[51] Int. Cl.$^5$ .................. C07D 209/02; A61K 31/40
[52] U.S. Cl. .................................... 514/412; 548/452
[58] Field of Search ......................... 548/453; 514/412

[56] References Cited

U.S. PATENT DOCUMENTS 4,849,524 7/1989 Henning et al.
4,868,307 9/1989 Barton et al.
4,886,827 12/1989 Urbach et al.

FOREIGN PATENT DOCUMENTS 243645 11/1987 European Pat. Off.
87/2230 5/1987 South Africa.

*Primary Examiner*—David B. Springer
*Attorney, Agent, or Firm*—Finnegan, Henderson, Farabow, Garrett, and Dunner

[57] ABSTRACT

Compounds with a psychotropic action, agents containing them, and the use thereof for the treatment and prophylaxis of disorders of the central nervous system.

The invention relates to the use of angiotensin converting enzyme inhibitors as pharmaceuticals with a psychotropic, especially anxiolytic, action, to agents containing them, and to the use thereof for the treatment or prophylaxis of disorders of the central nervous system, especially of anxiety states.

The invention also relates to new compounds of the formula

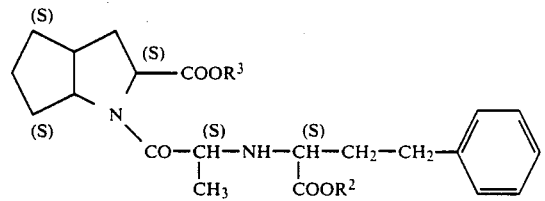

in which $R^2$ denotes hydrogen or ethyl, and $R^3$ denotes n-octyl, to processes for the preparation thereof, to agents containing them, and to the use thereof as pharmaceuticals.

6 Claims, No Drawings

COMPOUNDS WITH A PSYCHOTROPIC ACTION, AGENTS CONTAINING THEM, AND THE USE THEREOF FOR THE TREATMENT AND PROPHYLAXIS OF DISORDERS OF THE CENTRAL NERVOUS SYSTEM

The invention relates to the use of angiotensin converting enzyme inhibitors (ACE inhibitors) or the physiologically tolerated salts thereof as pharmaceuticals having a psychotropic, especially anxiolytic, action, to agents containing them, and to the use thereof for the preparation of appropriate pharmaceutical compositions.

Examples of compounds suitable for this novel use are those of the formula I $$X^1-X^2 \qquad (I)$$

in which
$X^1$ denotes

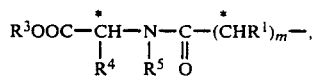

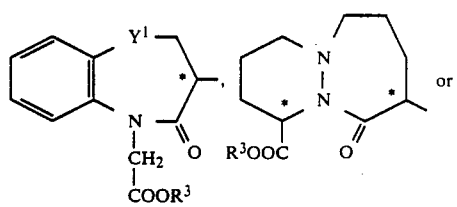

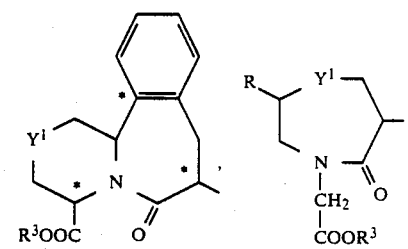

$X^2$ denotes
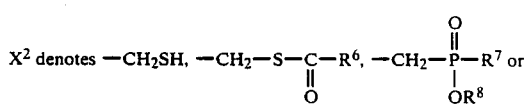

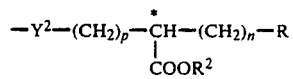

$Y^1$ represents —S— or —CH$_2$—,
$Y^2$ represents —NR$^9$— or —CH$_2$—,
m is 0 or 1,
n is 0, 1 or 2,
p is 0 or 1,
R denotes hydrogen, an optionally substituted aliphatic radical having 1-21 carbon atoms, an optionally substituted alicyclic radical having 3-20 carbon atoms, an optionally substituted aromatic radical having 6-12 carbon atoms, an optionally substituted araliphatic radical having 7-32 carbon atoms, an optionally substituted alicyclic-aliphatic radical having 4-20 carbon atoms, an optionally substituted heteroaromatic or heteroaromatic-($C_1$-$C_8$)-aliphatic radical having 5-12 ring atoms, or a radical $OR^a$ or $SR^a$, in which $R^a$ represents an optionally substituted aliphatic radical having 1-4 carbon atoms, an optionally substituted aromatic radical having 6-12 carbon atoms or an optionally substituted heteroaromatic radical having 5-12 ring atoms, $R^1$ denotes hydrogen, an optionally substituted aliphatic radical having 1-21 carbon atoms, an optionally substituted alicyclic radical having 3-20 carbon atoms, an optionally substituted alicyclic-aliphatic radical having 4-20 carbon atoms, an optionally substituted aromatic radical having 6-12 carbon atoms, an optionally substituted araliphatic radical having 7-32 carbon atoms, an optionally substituted heteroaromatic or heteroaromatic-($C_1$-$C_8$)-aliphatic radical having 5-12 ring atoms or, if not already covered by the above-mentioned definitions, the side-chain, which is protected where necessary, of a naturally occurring α-amino acid, $R^2$ and $R^3$ are identical or different and denote hydrogen, an optionally substituted aliphatic radical having 1-21 carbon atoms, an optionally substituted alicyclic radical having 3-20 carbon atoms, an optionally substituted aromatic radical having 6-12 carbon atoms, an optionally substituted araliphatic radical having 7-32 carbon atoms, a radical of the formula

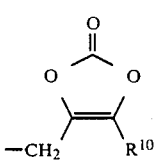

in which $R^{10}$ denotes hydrogen, an aliphatic radical having 1-6 carbon atoms or an optionally substituted aromatic radical having 6-12 carbon atoms, or denote a radical of the formula

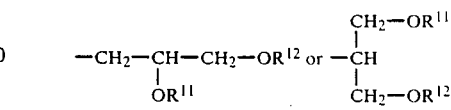

in which $R^{11}$ and $R^{12}$ denote, identically or differently and independently of one another, hydrogen, an optionally substituted alkyl radical having 1-23 carbon atoms or an optionally substituted acyl radical having 1-23 carbon atoms, $R^4$ represents hydrogen or ($C_1$-$C_6$)-alkyl, and
$R^5$ represents ($C_1$-$C_6$)-alkyl, ($C_3$-$C_6$)-cycloalkyl or

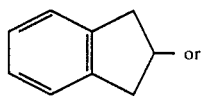

$R^4$ and $R^5$ form, together with the atoms carrying them, a mono-, bi- or tricyclic heterocyclic ring system having 3 to 15 ring carbon atoms, $R^6$ denotes hydrogen, amino, ($C_1$-$C_6$)-alkyl, ($C_6$-$C_{12}$)-aryl or ($C_7$-$C_{13}$)-aralkyl, $R^7$ denotes ($C_1$-$C_6$)-alkyl or ($C_7$-$C_{13}$)-aralkyl, preferably —(CH$_2$)$_4$—C$_6$H$_5$, $R^8$ denotes ($C_1$-$C_6$)-alkyl which is optionally monosubstituted by ($C_1$-$C_6$)-alkanoyloxy, preferably 2-methyl-1-propionyloxypropyl, and $R^9$ denotes hydrogen or ($C_1$-$C_6$)-alkyl; especially compounds of the formula II,

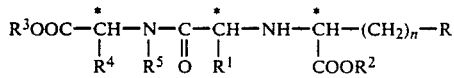 (II)

in which n is 1 or 2,

R denotes hydrogen, an optionally substituted aliphatic radical having 1–21 carbon atoms, an optionally substituted alicyclic radical having 3–20 carbon atoms, an optionally substituted aromatic radical having 6–12 carbon atoms, an optionally substituted araliphatic radical having 7–32 carbon atoms, an optionally substituted alicyclic-aliphatic radical having 7–14 carbon atoms, an optionally substituted heteroaromatic or heteroaromatic-($C_1$–$C_8$)-aliphatic radical having 5–12 ring atoms, or a radical $OR^a$ or $SR^a$, in which $R^a$ represents an optionally substituted aliphatic radical having 1–4 carbon atoms, an optionally substituted aromatic radical having 6–12 carbon atoms or an optionally substituted heteroaromatic radical having 5–12 ring atoms, $R^1$ denotes hydrogen, an optionally substituted aliphatic radical having 1–21 carbon atoms, an optionally substituted alicyclic radical having 3–20 carbon atoms, an optionally substituted alicyclic-aliphatic radical having 4–20 carbon atoms, an optionally substituted aromatic radical having 6–12 carbon atoms, an optionally substituted araliphatic radical having 7–32 carbon atoms, an optionally substituted heteroaromatic or heteroaromatic-($C_1$–$C_8$)-aliphatic radical having 5–12 ring atoms or, if not already covered by the abovementioned definitions, the side-chain, which is protected where necessary, of a naturally occurring α-amino acid, $R^2$ and $R^3$ are identical or different and denote hydrogen, an optionally substituted aliphatic radical having 1–21 carbon atoms, an optionally substituted alicyclic radical having 3–20 carbon atoms, an optionally substituted aromatic radical having 6–12 carbon atoms, an optionally substituted araliphatic radical having 7–32 carbon atoms, a radical of the formula

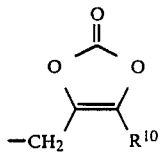

in which $R^{10}$ denotes hydrogen, an aliphatic radical having 1–6 carbon atoms or an optionally substituted aromatic radical having 6–12 carbon atoms, or denote a radical of the formula

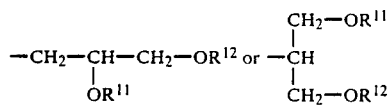

in which $R^{11}$ and $R^{12}$ denote, identically or differently and independently of one another, hydrogen, an optionally substituted alkyl radical having 1–23 carbon atoms or an optionally substituted acyl radical having 1–23 carbon atoms, and $R^4$ and $R^5$ form, together with the atoms carrying them, a mono-, bi- or tricyclic heterocyclic ring system having 3 to 15 ring carbon atoms.

An optionally substituted aliphatic radical is defined as an aliphatic acyclic radical, i.e. a radical having an open straight or branched carbon chain such as, for example, alkyl, alkenyl, alkynyl and corresponding polyunsaturated radicals. It is preferably unsubstituted or monosubstituted as described below for, for example, carboxyl, carbamoyl, aminoalkyl, alkanoylaminoalkyl, alkoxycarbonylaminoalkyl, arylalkoxycarbonylaminoalkyl, arylalkylaminoalkyl, alkylaminoalkyl, dialkylaminoalkyl, alkylthioalkyl, arylthioalkyl, carboxyalkyl, carbamoylalkyl, alkoxycarbonylalkyl, alkanoyloxyalkyl, alkoxycarbonyloxyalkyl, aroyloxyalkyl or aryloxycarbonyloxyalkyl.

An optionally substituted alicyclic radical, and the corresponding optionally substituted alicyclic-aliphatic radical bonded via an open carbon chain, is a preferably mono- to pentacyclic isocyclic, non-aromatic radical which has single bonds or unsymmetrically distributed double bonds and can also be branched (i.e. carry open-chain aliphatic side-chains) and is linked via a ring carbon atom or a side-chain carbon atom. It is preferably unsubstituted. Several rings as components of a radical of these types, fused, spiro-linked or isolated. Examples of radicals of these types are cycloalkyl, cycloalkenyl, cycloalkyl alkyl, bicycloalkyl, tricycloalkyl and radicals derived from mono-, bi- or oligocyclic terpenes, such as menthyl, isomenthyl, bornyl, caranyl, epibornyl, epiisobornyl, isobornyl, neomenthyl, neoisomenthyl, pinanyl and thujanyl; they are preferably unsubstituted (aliphatic side-chains are not substituents according to the present definition).

An optionally substituted aromatic radical is preferably aryl such as phenyl, biphenylyl or naphthyl, which is optionally mono-, di- or trisubstituted as indicated below for aryl(b)5.). Radicals derived from aryl, such as aralkyl, aryloxy, arylthio or aroyl, preferably benzoyl, can be substituted as aryl.

An optionally substituted heteroaromatic radical is preferably an aromatic mono- or bicyclic heterocyclic radical having, respectively, 5 to 7 or 8 to 12, preferably up to 10, ring atoms, 1 or 2 of these ring atoms representing sulfur or oxygen atoms and/or 1 to 4 of these ring atoms representing nitrogen atoms, such as, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated. A heteroaromatic radical, and the corresponding heteroaromatic-aliphatic radical, can be substituted as defined below.

An optionally substituted araliphatic radical is defined as, in particular, aralkyl radicals such as arylalkyl, diarylalkyl, indanyl or fluorenyl, in which aryl is as defined above and can be substituted in the manner indicated there.

An optionally substituted acyl radical is a straight-chain or branched, saturated or unsaturated aliphatic radical, preferably an unsubstituted saturated or unsaturated alkanoyl radical, such as formyl, acetyl, propionyl, butyryl, isobutyryl, valeryl, isovaleryl, pivaloyl, lauroyl, myristoyl, palmitoyl, stearoyl, hexanoyl, octanoyl, decanoyl, arachidonoyl, sorboyl, angeloyl, acryloyl, propiolyl, methacryloyl, crotonoyl, isocrotonoyl, oleoyl, elaidoyl or ricinoleoyl. Fatty acid radicals as occur in natural triglycerides are preferred.

$R^4$ and $R^5$ can form, with the atoms carrying them, a mono-, bi- or tricyclic heterocyclic ring system which has 3 to 15 ring carbon atoms and has in the ring preferably up to 2 sulfur atoms and up to 2 nitrogen atoms, in particular up to 1 sulfur atom.

Suitable ring systems of these types are those of the following group, in particular:

Pyrrolidine (O); thiazolidine (R); tetrahydroisoquinoline (A); decahydroisoquinoline (B); octahydroindole (C); indoline (O); octahydrocyclopenta[b]pyrrole (D); 2-azaspiro[4.5]decane (E); 2-azaspiro[4.4]nonane (F); spiro[(bicyclo[2.2.1]heptane)-2,3'-pyrrolidine] (G); spiro[(bicyclo[2.2.2]octane)-2,3'-pyrrolidine] (H); 2-azatricyclo[4.3.0.1$^{6,9}$]decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); 1,2,3,3a,4,6a-hexahydrocyclopenta[b]pyrrole (P), all of which can optionally be substituted. Pyrrolidine (O) and thiazolidine (R) can be monosubstituted by, for example, ($C_6$–$C_{12}$)-aryl (inter alia phenyl and 2-hydroxyphenyl), ($C_6$–$C_{12}$)-arylmercapto (such as phenylmercapto) or ($C_3$–$C_7$)-cycloalkyl (such as cyclohexyl). Tetrahydroisoquinoline (A) can carry, for example, in the aryl moiety up to 2 ($C_1$–$C_6$)-alkoxy radicals, preferably methoxy radicals. Corresponding statements apply to the other ring systems. However, the unsubstituted systems are preferred.

Suitable heterocyclic ring systems have the following structural formulae:

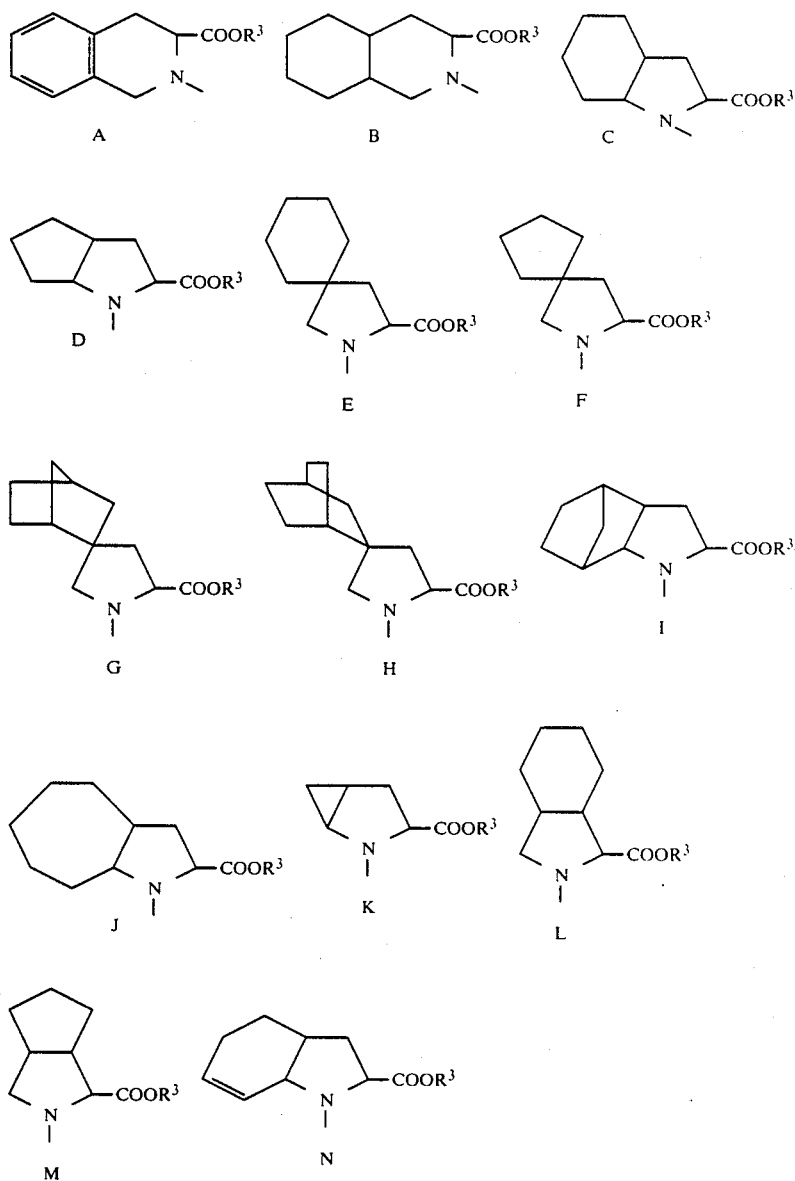

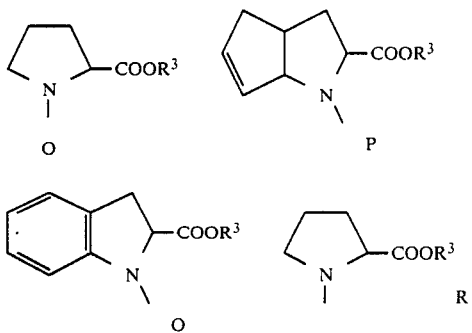

Examples of naturally occurring α-amino acids are Ala, Ser, Thr, Val, Leu, Ile, Asp, Asn, Glu, Gln, Arg, Lys, Hyl, Orn, Cit, Tyr, Phe, Trp and His.

If $R^1$ represents a side-chain of a protected naturally occurring α-amino acid, such as, for example, protected Ser, Thr, Asp, Asn, Glu, Gln, Arg, Lys, Hyl, Cys, Orn, Cit, Tyr, Trp or His, the preferred protective groups are the groups customary in peptide chemistry (cf. Houben-Weyl, Vol. XV/1 and XV/2). Where $R^1$ denotes the protected lysine side-chain, the known amino protective groups are preferred, but especially Z, Boc or $(C_1-C_6)$-alkanoyl. Suitable and preferred 0 protective groups for tyrosine are $(C_1-C_6)$-alkyl, especially methyl or ethyl.

The compounds of the formula I or II have asymmetric carbon atoms and can thus occur as enantiomers and diastereomers. The invention embraces both the pure enantiomers and the racemates.

In the case of compounds of the formula I or II which have several chiral atoms, all the possible diastereomers, as racemates or enantiomers, or mixtures of various diastereomers, are suitable.

A preferred embodiment comprises use of compounds of the formula I, preferably those of the formula II, in which (a) n is 1 or 2;
(b) R
1. denotes hydrogen;
2. denotes alkyl having 1-18 carbon atoms;
3. denotes an aliphatic acyclic radical of the formula $C_aH_{(2a-b+1)}$, in which double bonds are, if their number exceeds 1, not cumulative, and a represents an integer 2 to 18 and b represents an integer 2 to a;
4. denotes a mono-, di-, tri-, tetra- or pentacyclic non-aromatic hydrocarbon radical of the formula $C_cH_{(2c-d-1)}$, which is optionally branched and in which c represents an integer 3 to 20 and d represents an even number 0 to (c−2);
5. denotes aryl which has 6-12 carbon atoms and can be mono-, di- or trisubstituted by $(C_1-C_8)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl;
6. if n is 2, denotes $(C_6-C_{12})$-aryl-$(C_1-C_8)$-alkyl or di-$(C_6-C_{12})$-aryl-$(C_1-C_8)$-alkyl, each of which can be substituted in the aryl moiety as described under (b)5.; or denotes
7. alkoxy having 1-4 carbon atoms;
8. aryloxy which has 6-12 carbon atoms and can be substituted as described under (b)5.;
9. mono- or bicyclic heteroaryloxy or heteroaryl-$(C_1-C_8)$-alkyl which has, respectively, 5-7 or 8-10 ring atoms, up to 9 of these ring atoms representing carbon and 1 or 2 of these ring atoms representing sulfur or oxygen and/or 1 to 4 of these ring atoms representing nitrogen, and which can be substituted in the heteroaryl as described under (b)5.;
10. amino-$(C_1-C_8)$-alkyl;
11. $(C_1-C_4)$-alkanoylamino-$(C_1-C_8)$-alkyl;
12. $(C_7-C_{13})$-aroylamino-$(C_1-C_8)$-alkyl;
13. $(C_1-C_4)$-alkoxy-carbonylamino-$(C_1-C_8)$-alkyl;
14. $(C_6-C_{12})$-aryl-$(C_1-C_4)$-alkoxycarbonylamino-$(C_1-C_8)$-alkyl;
15. $(C_6-C_{12})$-aryl-$(C_1-C_4)$-alkylamino-$(C_1-C_8)$-alkyl;
16. $(C_1-C_4)$-alkylamino-$(C_1-C_8)$-alkyl;
17. di-$(C_1-C_4)$-alkylamino-$(C_1-C_8)$-alkyl;
18. guanidino-$(C_1-C_8)$-alkyl;
19. imidazolyl,
20. indolyl;
21. $(C_1-C_4)$-alkylthio;
22. if n is 2, $(C_1-C_4)$-alkylthio-$(C_1-C_8)$-alkyl;
23. $(C_6-C_{12})$-arylthio-$(C_1-C_8)$-alkyl which can be substituted in the aryl moiety as described under (b)5.;
24. $(C_6-C_{12})$-aryl-$(C_1-C_8)$-alkylthio, which can be substituted in the aryl moiety as described under (b)5.;
25. if n is 2, carboxy-$(C_1-C_8)$-alkyl;
26. carboxyl;
27. carbamoyl;
28. if n is 2, carbamoyl-$(C_1-C_8)$-alkyl;
29. $(C_1-C_4)$-alkoxy-carbonyl-$(C_1-C_8)$-alkyl;
30. if n is 2, $(C_6-C_{12})$-aryloxy-$(C_1-C_8)$-alkyl which can be substituted in the aryl moiety as described under (b)5.; or
31. $(C_6-C_{12})$-aryl-$(C_1-C_8)$-alkoxy which can be substituted in the aryl moiety as described under (b)5.;
(c) $R^1$
1. denotes hydrogen;
2. denotes alkyl having 1-18 carbon atoms;
3. denotes an aliphatic radical of the formula $C_aH_{(2a-b+1)}$, in which double bonds are, if their number exceeds 1, not cumulative, and a represents an integer 2 to 18 and b represents an even number 2 to a;
4. denotes a mono-, di-, tri-, tetra- or pentacyclic non-aromatic hydrocarbon radical of the formula $C_cH_{(2c-d-1)}$, which is optionally branched and in which c represents an integer 3 to 20 and d represents an even number 0 to (c−2);
5. aryl which has 6-12 carbon atoms and can be substituted as described under (I.b)5.;

6. $(C_6-C_{12})$-aryl-$(C_1-C_8)$-alkyl or $(C_7-C_{13})$-aroyl-$(C_1-C_8)$-alkyl both of which can be substituted in the aryl moiety as described under (b)5.;
7. mono- or bicyclic, optionally partially hydrogenated heteroaryl or heteroaryl-$(C_1-C_8)$-alkyl which has, respectively, 5-7 or 8-10 ring atoms, up to 9 of these ring atoms representing carbon and 1 or 2 of these ring atoms representing sulfur or oxygen and/or 1 to 4 of these ring atoms representing nitrogen, and which can be substituted in the heteroaryl as described for aryl under (b)5.; or
8. if not yet covered by (c)1.-7., denotes the optionally protected side-chain of a naturally occurring α-amino acid of the formula $R^1$—CH(NH$_2$)—COOH;

(d) $R^2$ and $R^3$ are identical or different and
1. denotes hydrogen;
2. alkyl having 1-18 carbon atoms;
3. denotes an aliphatic acyclic radical of the formula $C_aH_{(2a-b+1)}$, in which double bonds are, if their number exceeds 1, not cumulative, and a represents an integer 2 to 18 and b represents an even number 2 to a;
4. denotes a mono-, di-, tri-, tetra- or pentacyclic non-aromatic hydrocarbon radical of the formula $C_cH_{(2c-d-1)}$, which is optionally branched and in which c represents an integer 3 to 20 and d represents an even number 0 to (c−2);
5. di-$(C_1-C_4)$-alkylamino-$(C_1-C_8)$-alkyl;
6. $(C_1-C_5)$-alkanoyloxy-$(C_1-C_8)$-alkyl;
7. $(C_1-C_6)$-alkoxy-carbonyloxy-$(C_1-C_8)$-alkyl;
8. $(C_7-C_{13})$-aroyloxy-$(C_1-C_8)$-alkyl;
9. $(C_6-C_{12})$-aryloxycarbonyloxy-$(C_1-C_8)$-alkyl;
10. aryl having 6-12 carbon atoms;
11. $(C_7-C_{20})$-aralkyl;
12. phthalidyl;
13. denotes a radical of the formula

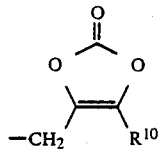

in which $R^{10}$ is hydrogen, $(C_1-C_6)$-alkyl or aryl having 6-12 carbon atoms,
14. denotes a radical of the formula

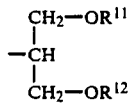

in which $R^{11}$ and $R^{12}$ denote, identically or differently and independently of one another, hydrogen, an optionally substituted alkyl radical having 1-23 carbon atoms or an optionally substituted acyl radical having 1-23 carbon atoms, it being possible for the radicals mentioned under (d)8., 9., 10. and 11. to be substituted in the aryl moiety as described under (b)5.; and (e) $R^4$ and $R^5$ form, together with the atoms carrying them, a mono-, bi- or tricyclic heterocyclic ring system having 3 to 15 ring carbon atoms.

A particularly preferred embodiment comprises use of compounds of the formula I, preferably those of the formula II, in which n is 1 or 2,
R denotes hydrogen, alkyl having 1-8 carbon atoms, alkenyl having 2-6 carbon atoms, cycloalkyl having 3-9 carbon atoms, aryl which has 6-12 carbon atoms and can be mono-, di- or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl, or denotes alkoxy having 1-4 carbon atoms, aryloxy which has 6-12 carbon atoms and can be substituted as described above for aryl, mono- or bicyclic heteroaryloxy which has, respectively, 5-7 or 8-10 ring atoms, 1 or 2 of these ring atoms representing sulfur or oxygen atoms and/or 1 to 4 of these ring atoms representing nitrogen, and which can be substituted as described above for aryl,
amino-$(C_1-C_4)$-alkyl,
$(C_1-C_4)$-alkanoylamino-$(C_1-C_4)$-alkyl,
$(C_7-C_{13})$-aroylamino-$(C_1-C_4)$-alkyl
$(C_1-C_4)$-alkoxy-carbonylamino-$(C_1-C_4)$-alkyl,
$(C_6-C_{12})$-aryl-$(C_1-C_4)$-alkoxycarbonylamino-$(C_1-C_4)$-alkyl
$(C_6-C_{12})$-aryl-$(C_1-C_4)$-alkylamino-$(C_1-C_4)$-alkyl,
$(C_1-C_4)$-alkylamino-$(C_1-C_4)$-alkyl,
di-$(C_1-C_4)$-alkylamino-$(C_1-C_4)$-alkyl,
guanidino-$(C_1-C_4)$-alkyl,
imidazolyl, indolyl,
$(C_1-C_4)$-alkylthio,
$(C_1-C_4)$-alkylthio-$(C_1-C_4)$-alkyl,
$(C_6-C_{12})$-arylthio-$(C_1-C_4)$-alkyl, which can be substituted in the aryl moiety as described above for aryl,
$(C_6-C_{12})$-aryl-$(C_1-C_4)$-alkylthio, which can be substituted in the aryl moiety as described above for aryl,
carboxy-$(C_1-C_4)$-alkyl,
carboxyl, carbamoyl,
carbamoyl-$(C_1-C_4)$-alkyl,
$(C_1-C_4)$-alkoxy-carbonyl-$(C_1-C_4)$-alkyl,
$(C_6-C_{12})$-aryloxy-$(C_1-C_4)$-alkyl, which can be substituted in the aryl moiety as described above for aryl, or
$(C_6-C_{12})$-aryl-$(C_1-C_4)$-alkoxy, which can be substituted in the aryl moiety as described above for aryl, $R^1$ denotes hydrogen, alkyl having 1-6 carbon atoms, alkenyl having 2-6 carbon atoms, alkynyl having 2-6 carbon atoms, cycloalkyl having 3-9 carbon atoms, cycloalkenyl having 5-9 carbon atoms, $(C_3-C_9)$-cycloalkyl-$(C_1-C_4)$-alkyl, $(C_5-C_9)$-cycloalkenyl-$(C_1-C_4)$-alkyl, optionally partially hydrogenated aryl which has 6-12 carbon atoms and can be substituted as described above for R,
$(C_6-C_{12})$-aryl-$(C_1-C_4)$-alkyl or $(C_7-C_{13})$-aroyl-$(C_1$ or $C_2)$-alkyl both of which can be substituted as the preceding aryl, mono- or bicyclic, optionally partially hydrogenated heteroaryl which has, respectively, 5-7 or 8-10 ring atoms, 1 or 2 of these ring atoms representing sulfur or oxygen atoms and/or 1 to 4 of these ring atoms representing nitrogen atoms, and which can be substituted as the preceding aryl, or the optionally protected side-chain of a naturally occurring α-amino acid $R^1$—CH(NH$_2$)—COOH, $R^2$ and $R^3$ are identical or different and denote hydrogen, alkyl having 1-12 carbon atoms, alkenyl having 2-12 carbon atoms, di-$(C_1-C_4)$-alkylamino-$(C_1-C_8)$-alkyl, $(C_1-C_5)$-alkanoyloxy-$(C_1-C_8)$-alkyl, $(C_1-C_6)$-alkoxy-carbonyloxy-$(C_1-C_8)$-alkyl, $(C_7-C_{13})$-aroyloxy-$(C_1-C_8)$-alkyl, $(C_6-C_{12})$-aryloxycarbonyloxy-$(C_1-C_8)$-alkyl, aryl having 6-12 carbon atoms, $(C_6-C_{12})$-aryl-$(C_1-C_8)$-alkyl, $(C_3-C_9)$-cycloalkyl or $(C_3-C_9)$-cycloalkyl-$(C_1-C_8)$-alkyl, and R⁴ and R⁵ have the meaning indicated above.

A very particularly preferred embodiment comprises use of compounds of the formula I, preferably those of the formula II, in which n is 1 or 2, R denotes $(C_1-C_6)$-alkyl, $(C_2-C_6)$-alkenyl, $(C_3-C_9)$-cyclo-alkyl, amino-$(C_1-C_4)$-alkyl, $(C_2-C_5)$-acylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, or $(C_6-C_{12})$-aryl which can be mono-, di- or trisubstituted by $(C_1-C_4)$alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or denotes 3-indolyl, especially methyl, ethyl, cyclohexyl, tert.butoxycarbonylamino-$(C_1-C_4)$-alkyl, benzoyloxycarbonylamino-$(C_1-C_4)$-alkyl or phenyl which can be mono- or disubstituted, or in the case of methoxy trisubstituted, by phenyl, $(C_1-C_2)$-alkyl, $(C_1$ or $C_2)$-alkoxy, hydroxyl, fluorine, chlorine, bromine, amino, $(C_1-C_4)$-alkylamino, di-$(C_1-C_4)$-alkylamino, nitro and/or methylenedioxy, R¹ denotes hydrogen or $(C_1-C_6)$-alkyl which can optionally be substituted by amino, $(C_1-C_6)$-acylamino or benzoylamino or denotes $(C_2-C_6)$-alkenyl, $(C_3-C_9)$-cycloalkyl, $(C_5-C_9)$-cycloalkenyl, $(C_3-C_7)$-cycloalkyl-$(C_1-C_4)$-alkyl, $(C_6-C_{12})$-aryl or partially hydrogenated aryl, each of which can be substituted by $(C_1-C_4)$-alkyl, $(C_1$ or $C_2)$-alkoxy or halogen, or denotes $(C_6-C_{12})$-aryl-$(C_1$ to $C_4)$-alkyl or $(C_7-C_{13})$-aroyl-$(C_1-C_2)$-alkyl, both of which can be substituted in the aryl radical as defined above, a mono- or bicyclic heterocyclic radical having, respectively, 5 to 7 or 8 to 10 ring atoms, 1 or 2 of these ring atoms representing sulfur or oxygen atoms and/or 1 to 4 of these ring atoms representing nitrogen atoms, or a side-chain of a naturally occurring, optionally protected α-amino acid, but in particular hydrogen, $(C_1-C_3)$-alkyl, $(C_2$ or $C_3)$-alkenyl, the optionally protected side-chain of lysine, benzyl, 4-methoxybenzyl, 4-ethoxybenzyl, phenethyl, 4-aminobutyl or benzoylmethyl, R² and R³ denote identical or different radicals hydrogen, $(C_1-C_{12})$-alkyl, $(C_2-C_{12})$-alkenyl or $(C_6-C_{12})$-aryl-$(C_1-C_8)$-alkyl, and R⁴ and R⁵ have the meaning indicated above.

The following compounds can be used particularly advantageously according to the invention:

2-[N-(1-S-Carbethoxy-3-phenyl-propyl)-S-alanyl]-S-1,2,3,4-tetrahydroisoquinoline-3-carboxylic acid 2-[N-(1-S-Carbethoxy-3-cyclohexyl-propyl)-S-alanyl]-S-1,2,3,4-tetrahydroisoquinoline-3-carboxylic acid 2-[N-(1-S-Carbethoxy-3-phenyl-propyl)-S-lysyl]-S-1,2,3,4-tetrahydroisoquinoline-3-carboxylic acid 2-[N-(1-S-Carbethoxy-3-phenyl-propyl)-O-ethyl-S-tyrosyl]-S-1,2,3,4-tetrahydroisoquinoline-3-carboxylic acid 2-[N-(1-S-Carbethoxy-3-phenyl-propyl)-S-alanyl]-3S-decahydroisoquinoline-3-carboxylic acid 1-[N-(1-S-Carbethoxy-3-phenyl-propyl)-S-alanyl]-(2S,3aS,7aS)-octahydroindole-2-carboxylic acid 1-[N-(1-S-Carbethoxy-3-cyclohexyl-propyl)-S-alanyl]-(2S,3aS,7aS)-octahydroindole-2-carboxylic acid 1-[N-(1-S-Carbethoxy-3-phenyl-propyl)-S-lysyl]-(2S,3aS,7aS)-octahydroindole-2-carboxylic acid 1-[N-(1-S-Carbethoxy-3-cyclohexyl-propyl)-S-lysyl]-(2S,3aS,7aS)-octahydroindole-2-carboxylic acid 1-[N-(1-S-Carbethoxy-3-cyclohexyl-propyl)-S-lysyl]-(2S,3aS,7aS)-octahydroindole-2-carboxylic acid 1-[N-(1-S-Carbethoxy-3-phenyl-propyl)-O-methyl-S-tyrosyl]-(2S,3aS,7aS)-octahydroindole-2-carboxylic acid 1-[N-(1-S-Carbethoxy-3-phenyl-propyl)-O-ethyl-S-tyrosyl]-(2S,3aS,7aS)-octahydroindole-2-carboxylic acid 1-[N-(1-S-Carbethoxy-3-(3,4-dimethylphenyl-propyl)-S-alanyl]-(2S,3aS,7aS)-octahydroindole-2-carboxylic acid 1-[N-[1-S-Carbethoxy-3-(4-fluorophenyl)-propyl]-S-alanyl]-(2S,3aS,7aS)-octahydroindole-2-carboxylic acid 1-[N-[1-S-Carbethoxy-3-(4-methoxyphenyl)-propyl]-S-alanyl]-(2S,3aS,7aS)-octahydroindole-2-carboxylic acid 1-[N-[1-S-Carbethoxy-3-(3,4-dimethoxyphenyl)-propyl]-S-alanyl]-(2S,3aS,7aS)-octahydroindole-2-carboxylic acid 1-[N-(1-S-Carbethoxy-3-cyclopentylpropyl)-S-alanyl]-(2S,3aS,7aS)-octahydroindole-2-carboxylic acid 1-[N-(1-S-Carbethoxy-3-phenyl-propyl)-S-alanyl]-(2S,3aR,7aS)-octahydroindole-2-carboxylic acid 1-[N-(1-S-Carbethoxy-3-cyclohexyl-propyl)-S-alanyl]-(2S,3aR,7aS)-octahydroindole-2-carboxylic acid 1-[N-(1-S-Carbethoxy-3-phenyl-propyl)-S-lysyl]-(2S,3aR,7aS)-octahydroindole-2-carboxylic acid 1-[N-(1-S-Carbethoxy-3-cyclohexyl-propyl)-S-lysyl]-(2S,3aR,7aS)-octahydroindole-2-carboxylic acid 1-[N-(1-S-Carbethoxy-3-phenyl-propyl)-O-ethyl-S-tyrosyl]-(2S,3aS,7aR)-octahydroindole-2-carboxylic acid 1-[N-(1-S-Carbethoxy-3-phenyl-propyl)-S-alanyl]-(2S,3aR,7aR)-octahydroindole-2-carboxylic acid 1-[N-(1-S-Carbethoxy-3-phenyl-propyl)-S-lysyl]-(2S,3aR,7aS)-octahydroindole-2-carboxylic acid 1-[N-(1-S-Carbethoxy-3-cyclohexyl-propyl)-S-alanyl]-(2S,3aR,7aR)-octahydroindole-2-carboxylic acid 1-[N-(1-S-Carbethoxy-3-cyclohexyl-propyl)-O-ethyl-S-tryosyl]-(2S,3aR,7aR)-octahydroindole-2-carboxylic acid 1-[N-(1-S-Carbethoxy-3-phenyl-propyl)-S-alanyl]-(2S,3aS,7aR)-octahydroindole-2-carboxylic acid 1-[N-(1-S-Carbethoxy-3-phenyl-propyl)-O-ethyl-S-tyrosyl]-(2S,3aS,7aS)-octohydroindole-2-carboxylic acid 1-[N-(1-S-Carbethoxy-3,4-dimethylphenyl-propyl)-S-alanyl]-(2S,3aS,7aS)-octahydroindole-2-carboxylic acid 1-[N-[1-S-Carbethoxy-3-(4-fluorophenyl)-propyl]-S-alanyl]-(2S,3aS,7aS)-octahydroindole-2-carboxylic acid 1-[N-[1-S-Carbethoxy-3-(4-methoxyphenyl)-propyl]-S-alanyl]-(2S,3aS,7aS)-octahydroindole-2-carboxylic acid 1-[N-[1-S-Carbethoxy-3-(3,4-dimethoxyphenyl)-propyl]-S-alanyl]-(2S,3aS,7aS)-octahydroindole-2-carboxylic acid 1-[N-(1-S-Carbethoxy-3-cyclopentylpropyl)-S-alanyl]-(2S,3aS,7aS)-octahydroindole-2-carboxylic acid 2-[N-(1-S-Carbethoxy-3-phenyl-propyl)-S-alanyl]-cis-endo-2-azabicyclo[3.3.0]octane-3-S-carboxylic acid 2-[N-(1-S-Carbethoxy-3-phenyl-propyl)-S-lysyl]-cis-endo-2-azabicyclo[3.3.0]octane-3-S-carboxylic acid 2-[N-(1-S-Carbethoxy-3-cyclohexyl-propyl)-S-alanyl]-cis-endo-2-azabicyclo[3.3.0]octane-3-S-carboxylic acid 2-[N-(1-S-Carboxy-3-cyclohexyl-propyl)-S-alanyl]-cis-endo-2-azabicyclo[3.3.0]octane-3-S-carboxylic acid 2-[N-(1-S-Carbethoxy-butyl)-S-alanyl]-cis-endo-2-azabicyclo[3.3.0]octane-3-S-carboxylic acid
2-[N-(1-S-Carbethoxy-3-(3,4-dimethoxyphenylpropyl)-S-alanyl]-cis-endo-2-azabicyclo[3.3.0]octane-3-S-carboxylic acid
2-[N-(1-S-Carbethoxy-3-cyclopentyl-propyl)-S-alanyl]-cis-endo-azabicyclo-[3.3.0]octane-3-S-carboxylic acid
2-[N-(1-S-Carbethoxy-3-phenyl-propyl)-O-methyl-S-tyrosyl]-cis-endo-2-azabicyclo[3.3.0]octane-3-S-carboxylic acid
2-[N-(1-S-Carbethoxy-3-phenyl-propyl)-O-ethyl-S-tyrosyl]-cis-endo-2-azabicyclo[3.3.0]octane-3-S-carboxylic acid
2-[N-(1-S-Carbethoxy-3-(4-fluorophenyl-propyl)-S-alanyl]-cis-endo-2-azabicyclo[3.3.0]octane-3-S-carboxylic acid
2-[N-(1-S-Carbethoxy-3-(4-methoxyphenyl-propyl)-S-alanyl]-cis-endo-2-azabicyclo[3.3.0]octane-3-S-carboxylic acid
1-[N-(1-S-Carbethoxy-3-phenyl-propyl)-S-lysyl]-(2S,3aR,6aS)-octahydrocyclopenta[b]pyrrole-2-carboxylic acid
1-[N-(1-S-Carbethoxy-3-cyclohexylpropyl)-S-lysyl]-(2S,3aR,6aS)-octahydrocyclopenta[b]pyrrole-2-carboxylic acid
1-[N-(1-S-Carbethoxy-3-phenyl-propyl)-O-ethyl-S-tryosyl]-(2S,3aR,6aS)-octahydrocyclopenta[b]pyrrole-2-carboxylic acid
1-[N-(1-S-Carbethoxy-3-phenyl-propyl)-S-alanyl]-2-(2S,3aR,6aS)-octahydrocyclopenta[b]pyrrole-2-carboxylic acid
2-[N-(1-S-Carbethoxy-3-phenyl-propyl)-S-alanyl]-2-azaspiro[4.5]decane-3-S-carboxylic acid
2-[N-(1-S-Carbethoxy-3-phenyl-propyl)-O-ethyl-2-tryosyl]-2-azaspiro-[4.5]decane-3-S-carboxylic acid
2-[N-(1-S-Carbethoxy-3-phenyl-propyl)-S-lysyl]-2-azaspiro[4.5]decane-3-S-carboxylic acid
2-[N-(1-S-Carbethoxy-3-cyclohexylpropyl)-S-alanyl]-2-azaspiro[4.5]decane-3-S-carboxylic acid
2-[N-(1-S-Carbethoxy-3-cyclohexylpropyl)-S-lysyl]-2-azasprio[4.5]decane-3-S-carboxylic acid
2-[N-(1-S-Carbethoxy-3-phenyl-propyl)-S-alanyl]-2-azaspiro[4.4]nonane-3-S-carboxylic acid
2-[N-(1-S-Carbethoxy-3-phenyl-propyl)-O-ethyl-S-tyrosyl]-2-azaspiro[4.4]nonane-3-S-carboxylic acid
2-[N-(1-S-Carbethoxy-3-phenyl-propyl)-S-lysyl]-2-azaspiro[4.4]nonane-3S-carboxylic acid
2-[N-(1-S-Carbethoxy-3-cyclohexyl-propyl)-S-alanyl]-2-azaspiro[4.4]nonane-3-S-carboxylic acid
2-[N-(1-S-Carbethoxy-3-cyclopentyl-propyl)-S-alanyl]-2-azaspiro[4.4]nonane-3-S-carboxylic acid
2-[N-(1-S-Carbethoxy-3-cyclopentyl-propyl)-S-lysyl]-2-azaspiro[4.4]nonane-3-S-carboxylic acid
1'-[N-(1-S-Carbethoxy-3-phenyl-propyl)-S-alanyl]-spiro[bicyclo[2.2.1]heptane-2,3'-pyrrolindine]-5'-S-carboxylic acid
1'-[N-(1-S-Carbethoxy-3-phenyl-propyl)-O-ethyl-S-tyrosyl]-spiro[bicyclo[2.2.1]heptane-2,3'-pyrrolindine]-5'-S-carboxylic acid
1'-[N-(1-S-Carbethoxy-3-phenyl-propyl)-S-lysyl]-spiro[bicyclo[2.2.1]heptane-2,3'-pyrrolindine]-5'-S-carboxylic acid
1'-[N-(1-S-Carbethoxy-3-cyclohexyl-propyl)-S-alanyl]-spiro[bicyclo[2.2.1]heptane-2,3'-pyrrolindine]-5'-S-carboxylic acid
1'-[N-(1-S-Carbethoxy-3-cyclohexyl-propyl)-S-lysyl]-spiro[bicyclo[2.2.1]heptane-2,3'-pyrrolindine[-5'-S-carboxylic acid
1'-[N-(1-S-Carbethoxy-3-phenyl-propyl)-S-alanyl]-spiro[bicyclo[2.2.2]octane-2,3,'-pyrrolidine]-5'-S-carboxylic acid
1'-[N-(1-S-Carbethoxy-3-phenyl-propyl)-O-ethyl-tyrosyl]-spiro-[bicyclo[2.2.2]octane-2,3'-pyrrolidine]-5'-S-carboxylic acid
1'-[N-(1-S-Carbethoxy-3-phenyl-propyl)-S-lysyl]-spiro[bicyclo[2.2.2]octane-2,3'-pyrrolidine]-5'-S-carboxylic acid
1'-[N-(1-S-Carbethoxy-3-cyclohexyl-propyl)-S-alanyl]-spiro[bicyclo[2.2.2]octane-2,3'-pyrrolidine]-5'-S-carboxylic acid
2-[N-(1-S-Carbethoxy-3-phenyl-propyl)-S-alanyl]-2-azatricyclo[4.3.0.1$^{6,9}$]decane-3-S-carboxylic acid
2-[N-(1-S-Carbethoxy-3-phenyl-propyl)-O-ethyl-S-tyrosyl]-2-azatricyclo[4.3.0.1$^{6,9}$]decane-3-S-carboxylic acid
2-[N-(1-S-Carbethoxy-3-phenyl-propyl)-S-lysyl]-2-azatricyclo[4.3.0.1$^{6,9}$]decane-3-S-carboxylic acid
2-[N-(1-S-Carbethoxy-3-cyclohexyl-propyl)-S-alanyl]-2-azatricyclo[4.3.0.1$^{6,9}$]decane-3-S-carboxylic acid
2-[N-(1-S-Carbethoxy-3-cyclohexyl-propyl)-S-lysyl]-2-azatricyclo[4.3.0.1$^{6,9}$]decane-3-S-carboxylic acid
1-[N-(1-S-Carbethoxy-3-phenyl-propyl)-S-alanyl]-decahydrocyclohepta[b]pyrrole-2-S-carboxylic acid
1-[N-(1-S-Carbethoxy-3-phenyl-propyl)-O-ethyl-S-tyrosyl]-decahydrocyclohepta[b]pyrrole-2-S-carboxylic acid
1-[N-(1-S-Carbethoxy-3-phenyl-propyl)-S-lysyl]-decahydrocyclohepta[b]pyrrole-2-S-carboxylic acid
1-[N-(1-S-Carbethoxy-3-cyclohexyl-propyl)-S-alanyl]-decahydrocyclohepta[b]pyrrole-2-S-carboxylic acid
1-[N-(1-S-Carbethoxy-3-cyclohexyl-propyl)-S-lysyl]-decahydrocyclohepta[b]pyrrole-2-S-carboxylic acid
2-[N-(1-S-Carbethoxy-3-phenyl-propyl)-S-alanyl]-trans-octahydroisoindole-1-S-carboxylic acid
2-[N-(1-S-Carbethoxy-3-phenyl-propyl)-S-alanyl]-cis-octahydroisoindole-1-S-carboxylic acid
2-[N-(1-S-Carbethoxy-3-cyclohexyl-propyl)-S-alanyl]-trans-octahydroisoindole-1-S-carboxylic acid
2-[N-(1-S-Carbethoxy-3-cyclohexyl-propyl)-S-alanyl]-cis-octahydroisoindole-1-S-carboxylic acid
2-[N-(1-S-Carbethoxy-3-phenyl-propyl)-S-analyl]-cis-octahydrocyclopenta[c]pyrrole-1-S-carboxylic acid
benzyl 2-[N-(1-S-Carbethoxy-3-cyclohexyl-propyl)-S-alanyl]-cis-octahydrocyclopenta[c]pyrrole-1-S-carboxylate
2-[N-(1-S-Carbethoxy-3-cyclohexyl-propyl)-S-lysyl]-cis-octahydrocyclopenta[c]pyrrole-1-S-carboxylic acid
1-[N-(1-S-Carbethoxy-3-phenyl-propyl)-S-alanyl]-2,3,3a,4,5,7a-hexahydroindole-cis-endo-2-S-carboxylic acid
1-[N-(1-S-Carbethoxy-3-phenyl-propyl)-S-lysyl]-2,3,3a,4,5,7a-hexahydroindole-cis-endo-2-S-carboxylic acid
2-[N-(1-S-Carbethoxy-3-cyclohexyl-propyl)-S-lysyl]-2-azabicyclo]3.1.0]hexane-3-S-carboxylic acid
2-[N-(1-S-Carboxy-3-phenyl-propyl)-S-lysyl]-2-azabicyclo[3.1.0]hexane-cis-endo-3-S-carboxylic acid
2-[N-(1-S-Carbethoxy-3-cyclopentylpropyl)-S-alanyl]-2-azabicyclo[3.1.0]hexane-3-carboxylic acid
2-[N-(1-S-Carbethoxy-3-phenyl-propyl)-S-alanyl]-cis-endo-2-azabicyclo[3.1.0]-hexane-3-carboxylic acid
2-[N-(1-S-Carbethoxy-3-cyclohexyl-propyl)-S-alanyl]-cis-enco-2-azabicyclo[3.1.0]hexane-3-S-carboxylic acid 1'-[N-(1-S-carbethoxy-3-phenylpropyl)-S-alanyl]-(3'S,5'S)-spiro-bicyclo[2.2.2]-octane-2,3'-pyrrolidine-5'-carboxylic acid octyl 2-[N-(1-S-carbethoxy-3-phenylpropyl)-S-alanyl]-cis-endo-2-azabicyclo[3.3.0]octane-3-S-carboxylate decyl 2-[N-(1-S-carbethoxy-3-phenylpropyl)-S-alanyl]-cis-endo-2-azabicyclo[3.3.0]octane-3-S-carboxylate 5-nonyl 2-[N-(1-S-carbethoxy-3-phenylpropyl)-S-alanyl]-cis-endo-2-azabicyclo[3.3.0]octane-3-S-carboxylate octyl 2-[N-(1-S-octyloxy-3-phenylpropyl)-S-alanyl]-cis-endo-2-azabicyclo[3.3.0]octane-3-S-carboxylate benzhydryl 2-[N-(1-S-menthyloxy-3-phenylpropyl)-S-alanyl]-cis-endo-2-azabicyclo[3.3.0]octane-3-S-carboxylate These compounds can be prepared, for example, by the process described in German Patent Application P 33 33 455.2 in that the tert.butyl or benzyl derivatives described in the application are converted into the monocarboxylic acid derivatives in a known manner by acid or alkaline hydrolysis or by hydrogenolysis catalyzed by noble metals. The $N^\epsilon$-benzyloxycarbonyl protective group of the lysine derivatives is removed by hydrogenolysis catalyzed by noble metals.

The compounds of the general formula I or II can also be prepared, for example, using the esterification methods familiar to the expert (see, for example, Buehler, Pearson, Survey of Organic Syntheses, Vol. 1, New York 1970, pages 802–825; Houben-Weyl, Methoden der Organischen Chemie (Methods of Organic Chemistry), Volume E5, 1985, pages 656–773), for example by (a) reaction of a mono- or dicarboxylic acid of the general formula I or II, in which at least one of the radicals $R^2$ and $R^3$ denotes hydrogen, with an appropriate alcohol with acid catalysis (mineral acid or acid ion exchanger).

(b) Alkylation of a mono- or dicarboxylic acid of the general formula I or II, in which at least one of the radicals $R^2$ and $R^3$ denotes hydrogen, with a compound $R^2Z$ or $R^3Z$, in which Z denotes a leaving group which can be displaced nucleophilically (such as halogen or tosylate), in a polar protic or dipolar aprotic solvent in the presence of a base such as alkali metal hydroxide or alcoholate.

(c) Reaction of a mono- or dicarboxylic acid of the general formula I or II, in which at least one of the radicals $R^2$ and $R^3$ denotes hydrogen, with a diazoalkane in an inert organic solvent such as $CH_2Cl_2$.

The compounds listed above can easily be converted with physiologically tolerated acids or bases (in the case of mono- or dicarboxylic acids) into the corresponding salts (for example hydrochlorides, maleates, fumarates etc.), and the salts can be used according to the invention.

The compounds of the formula I and II are inhibitors of angiotensin converting enzyme (ACE) or are intermediates in the preparation of such inhibitors and can also be used to control high blood pressure of various etiologies. Some of the compounds of the formula I and II and processes for the preparation thereof are known, for example from U.S. Pat. No. 4,129,571, U.S. Pat. No. 4,374,829, EP-A 79,522, EP-A 79,022, EP-A 49,658, EP-A 51,301, U.S. Pat. No. 4,454,292, U.S. Pat. No. 4,374,847, EP-A 72,352, U.S. Pat. No.4,350,704, EP-A 50,800, EP-A 46,953, U.S. Pat. No. 4,344,949, EP-A 84,164, U.S. Pat. No. 4,470,972, EP-A 65,301 and EP-A 52,991. New compounds of the formula I and II are prepared in an analogous manner.

Orally active ACE inhibitors are also advantageous (some of the active substances already mentioned above), such as, for example, ramipril, enalapril(f), captopril(a), lisinopril(g), cilazapril(o), RHC 3659, CGS 13945, CGS 13928C(1), CGS 14824A(h), CI-906(j), zofenopril(e), fosenopril(p), alacepril CI-925(k), pentopril(q), CV 3317(m), indolapril(h), YS 980(b), fentiapril(c), pivopril(d), perindopril(i), MDL 27088(r), MDL 27788(s), RS-5142(t) and others. Orally active ACE inhibitors are described, for example in Brunner et al., J. Cardiovasc. Pharmacol. 7 (Suppl. I) [1985] S2-S11.

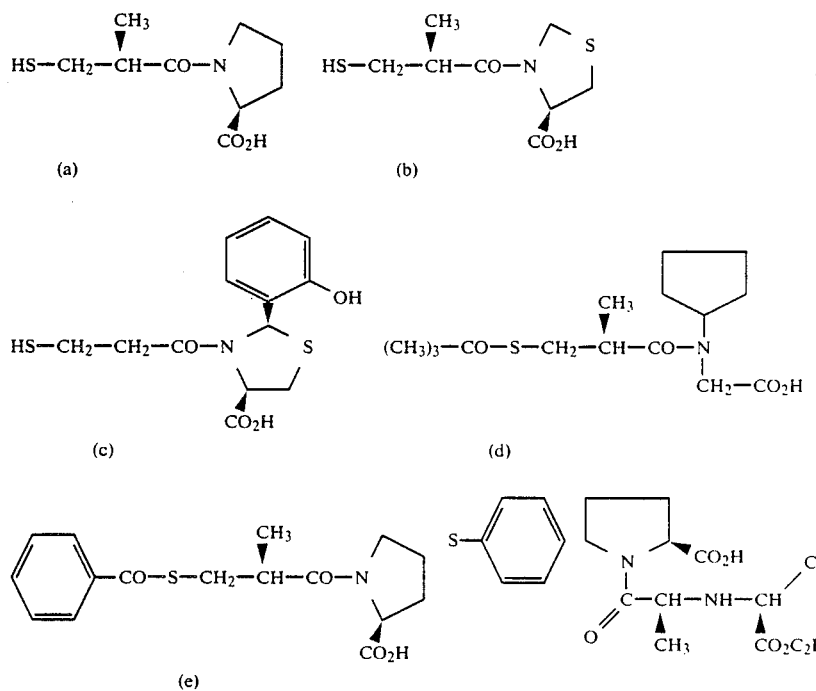

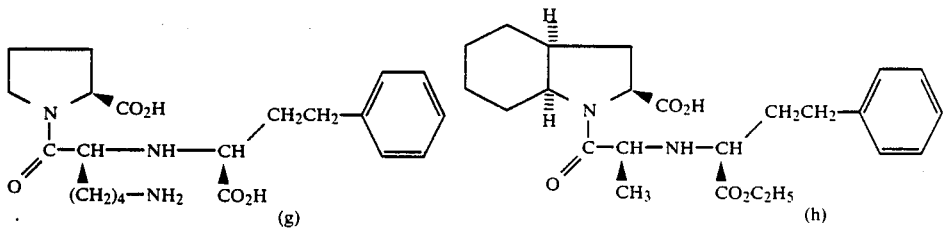
(g) (h)
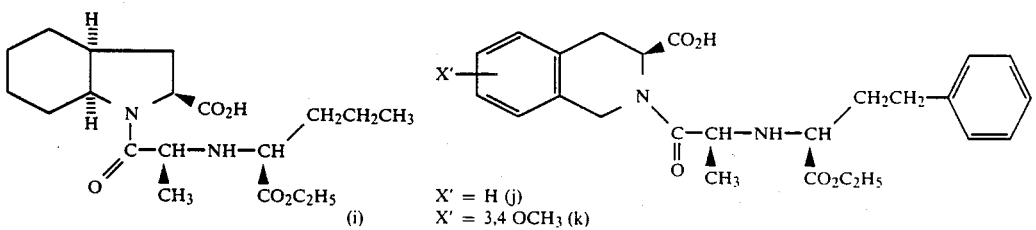
(i)　X' = H (j)　X' = 3,4 OCH₃ (k)
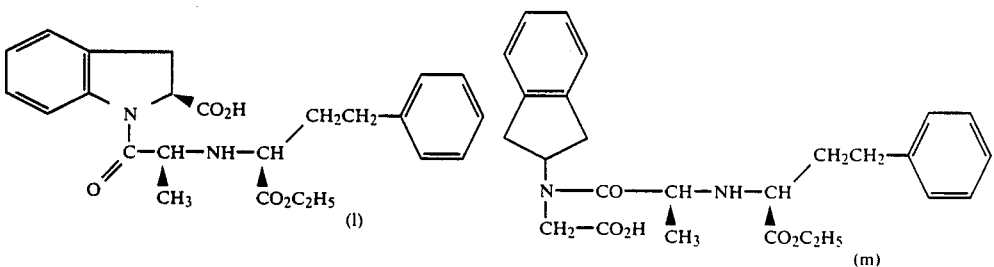
(l) (m)
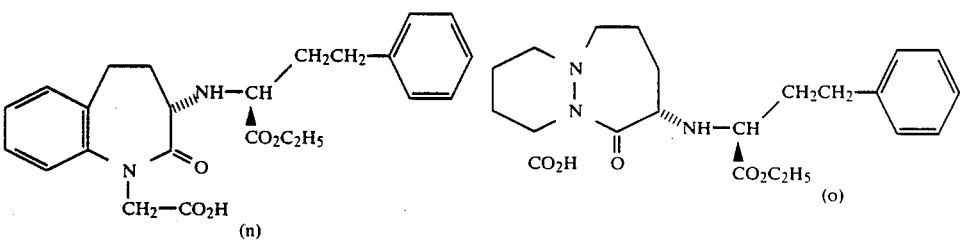
(n) (o)
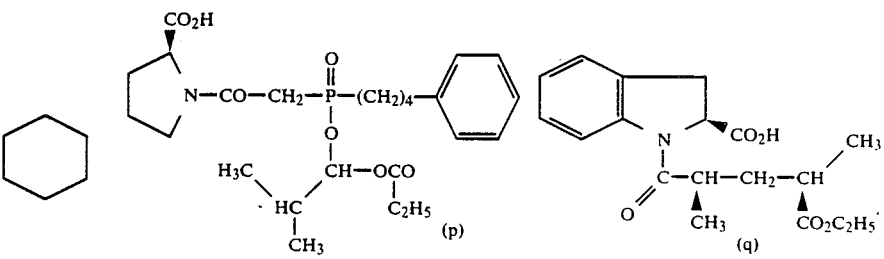
(p) (q)
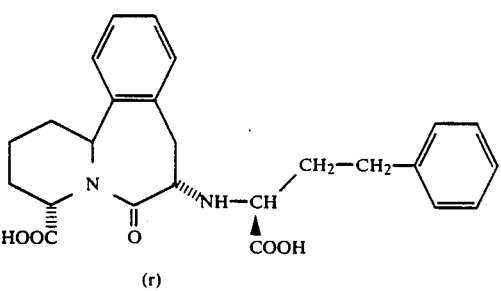
(r)

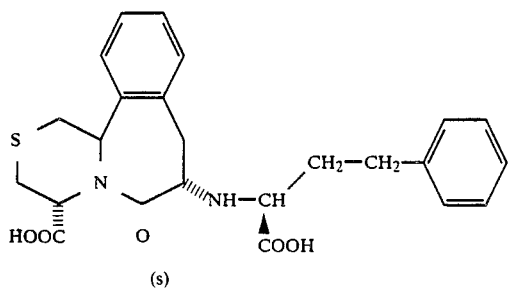

(s)

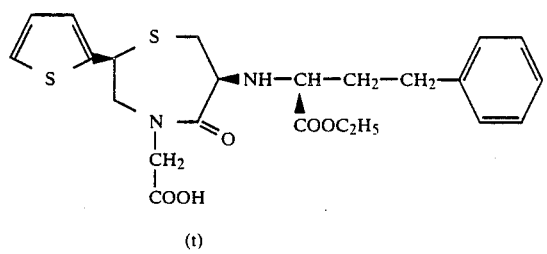

(t)

The preferred ACE inhibitors among those which are disclosed, inter alia, in EP-A 243645 and have the formula III

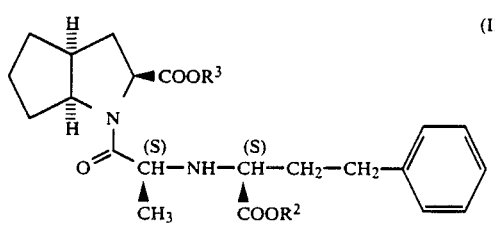

(III)

in which $R^2$ and $R^3$ are identical or different and denote hydrogen, an aliphatic radical having 1-21 carbon atoms, an alicyclic radical having 3-20 carbon atoms or an araliphatic radical having 7-32 carbon atoms, are those in which $R^2$ denotes hydrogen, methyl, ethyl, benzyl, menthyl or n-octyl, and $R^3$ denotes hydrogen, benzyhydryl, n-octyl, n-decyl or 5-nonyl.

Furthermore, preferred ACE inhibitors among those which are disclosed in EP-A 84164 and EP-A 243645 and have the formulae IVa and IVb

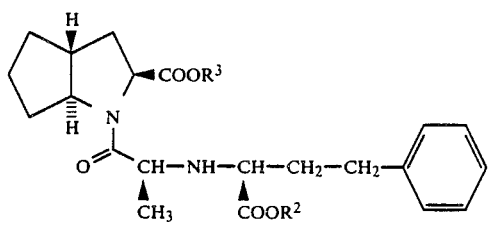

(IVa)

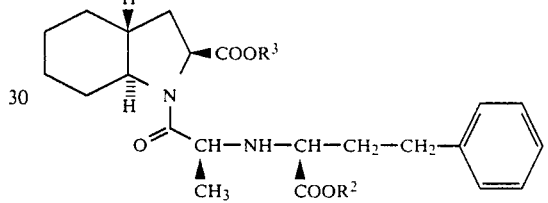

(IVb)

in which $R^2$ and $R^3$ are as defined above for formula III, are those in which $R^2$ denotes hydrogen, $(C_1-C_8)$-alkyl, benzyl or menthyl and $R^3$ denotes hydrogen, benzhydryl or $(C_1-C_{10})$-alkyl.

In addition, preferred ACE inhibitors are those which are disclosed in U.S. Pat. No. 4,620,012 and EP-A 243,645 and have the formula V

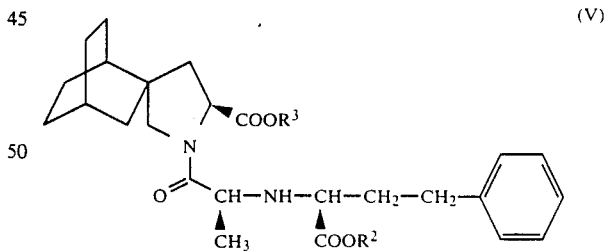

(V)

in which $R^2$ denotes hydrogen, $(C_1-C_8)$-alkyl, benzyl or menthyl and $R^3$ denotes hydrogen, benzhydryl or $(C_1-C_{10})$-alkyl, and the isomers thereof.

It is additionally disclosed in EP-A 243,645 that the compounds of the formula I and II additionally have a nootropic action (improving cognitive function) and thus are also suitable for the treatment of cognitive dysfunctions of various etiologies such as occur, for example, in Alzheimer's disease or in senile dementia.

It has now been found, surprisingly, that the compounds of the formula I and II have a psychotropic, in particular an anxiolytic, action. Hence they are suitable for the treatment and prophylaxis of disorders of the central nervous system, especially of anxiety states.

The anxiolytic action has been tested in various test models, for example in the lick-shock conflict test of VOGEL and in the "Geller-Seifter Conflict test" of GELLER and SEIFTER. Lick-shock conflict test Method (VOGEL, J. R., Psychopharmacologia 21, (1971), 1–7) Male Wistar rats bred by us (SPF Hattersheim) weighing between 90 and 120 g are used. Drinking water is withdrawn from the animals for 48 hours before the test starts. For the test, the animals are placed in a plastic box ($14 \times 12 \times 28$ cm, $W \times D \times H$) which is equipped with a water bottle with a metal drinking tube and additionally permits the number of contacts of the animal's tongue with the drinking tube to be measured via an electronic circuit. The floor of the box is made of metal rods through which a current can be passed by the electronic control system. After the animals have been placed in the box they are allowed 5 min to find the drinking tube and lick it 50 times. Animals which have not found the drinking tube within this time are not used for the test. After these 50 lickings, a current (direct current 300 $\mu A$) is passed through the drinking tube and floor rods for periods of 5 sec and then removed again for a further 5 sec.

This alternating sequence is continued for a period of 5 min, with the number of contacts made by the animal with the drinking tube during the periods with current and without current being recorded on various electronic counters.

Groups of eight animals for each dose are treated with the test substances by various routes of administration, for example orally, intraperitoneally or subcutaneously. In the case of oral administration by tube, the test substances are suspended in a 1% strength Tylose gel, and 5 ml/kg bodyweight is administered through the tube. The test is carried out in the abovementioned test apparatus 1 hour, in the case of oral administration, and 30 minutes, in the case of subcutaneous or intraperitoneal administration, after the test substances have been administered. The number of contacts with the drinking tube in the period with current serves as the test variable. The mean number of contacts in this period in the control group is set equal to 100%, and an increase or decrease in the number of contacts by the animals treated with the test substance is expressed as a percentage of that in the control group.

Anxiolytics usually bring about a distinct increase in the water intake (lickings), compared with the untreated controls, in the period with current in this test.

If there is a linear or logarithmic relation between the dose and the effect, an ED+100 (i.e. the dose which brings about an increase in the water intake by 100% compared with the control group) is calculated by means of regression analysis. If there is no linear dose-relationship, then a minimal effective dose (MED) is determined, i.e. the lowest dose of the test substance which still brings about a statistically significant increase in the water intake compared with the control group (p=0.05, DUNNETT test).

Number of contacts with the drinking tube in the period with current 30 minutes after administration of the test substance, compared with the control group

| Compound | Dose (mg/kg i.p.) | | | | | |
|---|---|---|---|---|---|---|
| | 0.1 | 0.3 | 1 | 3 | 10 | 30 |
| Captopril | | | | +46 | +109 | +117* |
| Analapril | | | | +42 | +114 | +130* |
| Ramipril | | | | +88 | +148* | +113 |
| A | | | | +1 | +32 | +65 |
| B | | | | +53 | +116* | +176* |
| C | +16 | +36/ +28 | +73/ +108* | +124 | | |

*p < 0.05 (Dunnett Test)

$$R^3OOC-CH-N-C-CH-NH-CH-(CH_2)_n-R \quad (II)$$
$$\phantom{R^3OOC-CH-N}R^4 \phantom{-}R^5 \phantom{-}O \phantom{-}R^1 \phantom{-CH-NH-CH}COOR^2$$

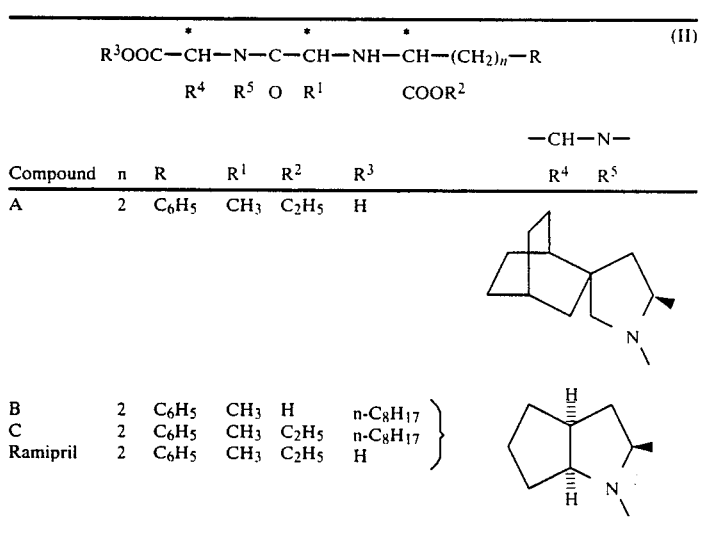

| Compound | n | R | $R^1$ | $R^2$ | $R^3$ | $-CH-N-$ $R^4 \phantom{xx} R^5$ |
|---|---|---|---|---|---|---|
| A | 2 | $C_6H_5$ | $CH_3$ | $C_2H_5$ | H | |
| B | 2 | $C_6H_5$ | $CH_3$ | H | n-$C_8H_{17}$ | |
| C | 2 | $C_6H_5$ | $CH_3$ | $C_2H_5$ | n-$C_8H_{17}$ | |
| Ramipril | 2 | $C_6H_5$ | $CH_3$ | $C_2H_5$ | H | |

Geller-Seifter conflict test

Method (Geller, I. and Seifter, J., Psychopharmacologia 1 (1962), 482):

Male Wistar rats bred by us (SPF Hattersheim) weighing between 240 and 370 g are used and are allocated to test groups each containing 8 animals. 4 Animals are placed together in each plastic cage ($56 \times 38 \times 20$ cm) and maintained at about 80% of their normal body weight by weighing the quantities of feed. The animals are trained to press a button in a SKINNER box and receive a reward in the form of sweetened condensed milk. The box contains two buttons with microswitches, a loudspeaker, an interior light, two signal lights above the buttons, and a floor made of metal rods. The training schedule was based on that of GELLER and SEIFTER (1962) as modified by DAVIDSON & COOK (Psychopharmacologia 15 (1969), 159–168): Each session comprises four 15-minute sections, all of which are composed of a 12-minute variable interval (VI) period and a 3-minute fixed ration (FR) period. During the VI period, the animals are rewarded for pressing the button by milk supplied after an interval, which is controlled by a random generator, of 10–110 sec. with a mean of 60±15 sec.

During the FR period, the animals receive a reward for each pressing of the button but, in addition, at each 3rd pressing of the button a painful electric shock is administered through the floor rods in order to generate a conflict situation. The current for the electric shock is adjusted individually for each animal (0.3–0.6 mA) so that the button is pressed between 5 and 15 times during the FR period.

Training takes place on 5 days a week, and tests are carried out on test substances once a week. Since the animals act as their own controls, at least two preliminary runs without test substance are carried out before each test with test substance. The compounds to be tested are suspended in 1% strength Tylose gel and are administered orally through a tube in a volume of 2 ml/kg 30 min before the test starts. Changes in the number of times the button is pressed in the VI period are regarded as an effect on motor activity, and increases in the number of times the button is pressed in the FR period are regarded as a sign of an "anticonflict" or "anxiolytic" action. Usually the minimal effective dose (MED) of the test substance is determined, i.e. the lowest tested dose which still brings about a statistically significant change in the number of times the button is pressed (p=0.05; WILCOXON matched pairs signed rank test).

The MEDs found after intraperitoneal administration in these two test models are between 0.1 and 30 mg/kg of test animal.

Hence the invention also relates to the use of the compounds according to the invention for the treatment and prophylaxis of disorders of the central nervous system, especially of anxiety states.

The invention additionally relates to new compounds of the formula III

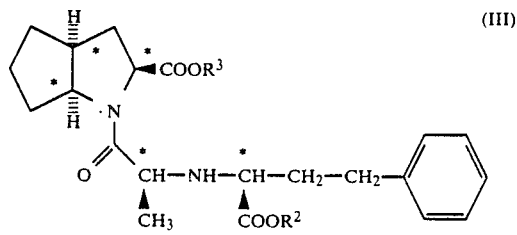

in which the five chiral carbon atoms (*) each have the S configuration, $R^2$ denotes ethyl or hydrogen, and $R^3$ denotes n-octyl, as well as the physiologically tolerated salts thereof, preferably the maleates.

One process according to the invention for the preparation of these new compounds comprises (a) reacting a compound of the formula III in which the five chiral carbon atoms (*) each have the S configuration, $R^2$ denotes ethyl or a carboxyl protective group which can be easily eliminated with base or acid or by hydrogenolysis, and $R^3$ denotes hydrogen, with n-octanol, preferably employing esterification methods familiar to the expert (see, for example, Buehler, Pearson, Survey of Organic Synthesis, Vol. 1, New York, 1970, pages 802–825; Houben-Weyl, Methoden der Organischen Chemie, volume E5, 1985, pages 656–773), for example under acid catalysis or after activation of the carboxyl group of III ($R^3$=H) or of the hydroxyl group of n-octanol, especially under the conditions of a Mitsunobu reaction, in a suitable solvent at a temperature up to the boiling point of the reaction mixture, or comprises (b) reacting a compound of the formula III in which the configuration and $R^2$ and $R^3$ are as defined above under (a) with a compound of the formula VI

in which X denotes a leaving group which can be displaced nucleophilically, especially a Cl, Br or I atom or a sulfonyl radical, under the conditions of a nucleophilic substitution, preferably in a polar organic solvent such as an alcohol, preferably methanol, ethanol, propanol or isopropanol, or a lower ketone, preferably acetone, methyl ethyl ketone or methyl isobutyl ketone, or in acetonitrile, dimethylformamide, dimethyl sulfoxide or sulfolane, or a hydrocarbon, preferably toluene, with or without the presence of an auxiliary base to capture the acid which is formed, preferably in the presence of potassium bicarbonate, sodium carbonate, triethylamine, pyridine, 1,5-diazabicyclo[5.4.0]undec-5-ene or 1,5-diazabicyclo[4.3.0]-non-5-ene, and with or without the presence of an alkali metal halide, preferably sodium iodide or potassium iodide, at a temperature between −50° and +100° C., preferably between −20° and +60° C., or comprises (c) reacting a compound of the formula III which has the configuration as above under (a), and in which $R^2$ denotes hydrogen and $R^3$ denotes n-octyl, with ethanol as described under process variant (a), or comprises (d) reacting a compound of the formula III in which the configuration, $R^2$ and $R^3$ are as defined above under (c) with a compound of the formula VII

in which X denotes a leaving group which can be displaced nucleophilically, as described under process variant (b), or comprises (e) reacting a compound of the formula VIII

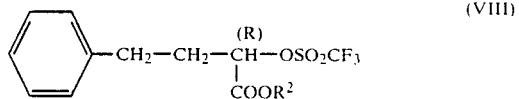

in which $R^2$ is as defined above under (a) with a compound of the formula IX

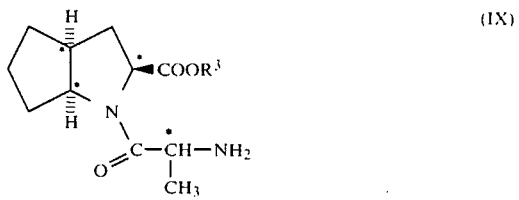

in which the four chiral carbon atoms (*) each have the S configuration, for example in analogy to the procedure described in U.S. Pat. No. 4,525,301, in a suitable solvent at a temperature up to the boiling point of the reaction mixture, or comprises (f) reacting a compound of the formula X

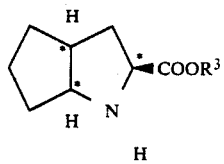

in which the three chiral carbon atoms (*) each have the S configuration, and $R^3$ denotes n-octyl, with a compound of the formula XI

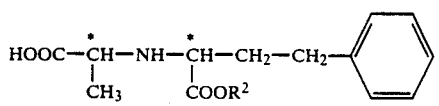

in which $R^2$ is as defined above under (a), for example in analogy to known peptide-coupling processes, in an organic solvent such as DMF, $CH_2Cl_2$ or DMA, in the presence of coupling aids such as carbodiimides (for example dicyclohexylcarbodiimide), diphenylphosphoryl azide, alkanephosphonic anhydrides, dialkylphosphinic anhydrides or $N^1,N$-disuccinimidyl carbonate in a solvent such as, for example, acetonitrile or after activation of the compounds of the formula X, for example by reaction with tetraethyl diphosphite or after conversion of the compounds of the formula XI into active esters (for example with 1-hydroxybenzotriazole), into mixed anhydrides (for example with chloroformic esters), into azides or into carbodiimide derivatives (cf. Schroder, Lubke, The Peptides, volume 1, New York 1965, pages 76-136) at temperatures preferably between $-20°$ C. and the boiling point of the solvent, where necessary eliminating the protective group $R^2$ in a resulting compound of the formula III ($R^2$=protective group), in a manner known per se, for example using hydrolysis methods familiar to the expert (such as acid or alkaline hydrolysis) or hydrogenation methods, in a suitable solvent, at a temperature up to the boiling point of the reaction mixture, and converting, where appropriate, the compound of the formula III ($R^2$=ethyl or hydrogen) obtained in this way into its physiologically tolerated salt, with, in the case where mixtures of stereoisomers are used as starting materials in process variants (a)-(f), subsequent removal, in another separation stage, of the all-S isomer of the formula III ($R^2$=hydrogen or ethyl, $R^3$=n-octyl).

A carboxyl protective group which can be eliminated by hydrogenolysis, such as Bzl, is preferably eliminated by hydrogenolysis on a suitable catalyst, such as, for example, palladium on active charcoal, under a pressure of 0.2 to 10 bar and at a temperature between $0°$ C. and $100°$ C. in an organic solvent.

Aliphatic radicals which can be easily removed by hydrolysis, such as ($C_1$-$C_6$)-alkyl, are the preferred carboxyl protective groups which can be eliminated with base or acid. They are eliminated using hydrolysis methods familiar to the expert (see, for example, Houben/Weyl, Methoden der Organischen Chemie, volume E 5/1, pages 223-255), for example by acid or alkaline hydrolysis.

The compounds of the formula III ($R^2$=hydrogen or ethyl, $R^3$=hydrogen) are known (see, for example, EP-A 79022, U.S. Pat. No. 4,587,258).

Compounds of the formula VI and VII are known, and most can be obtained commercially.

Compounds of the formula VIII are obtained from the corresponding hydroxyl compounds by conversion of the hydroxyl group into the $-OSO_2CF_3$ group by conventional processes.

It is possible to remove the abovementioned new all-S compounds from mixtures of diastereomers or enantiomers by recrystallization or by chromatography, for example on silica gel, or by salt formation using optically active auxiliaries.

The invention also relates to intermediates of the formula XII

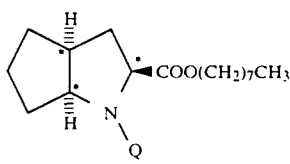

in which the three chiral carbon atoms each have the S configuration, and Q denotes hydrogen or the radical XIII

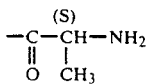

and to mixtures of compounds of the formula XII and the stereoisomers thereof, as well as to a process for the preparation of these compounds, which comprises (a) reacting a compound of the formula XIV

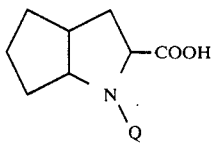

in which Q denotes hydrogen or $-CO-CH(CH_3)-NH_2$, with n-octanol or $H_3C-[CH_2]_7-X$, as above in process variant (a) or (b), or (b) reacting a compound of the formula XV

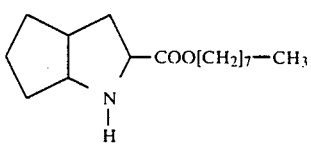

as above in process variant (f), with an amino-protected alanine, for example protected with Z or Boc, and subsequently eliminating the amino protective group and, if desired, isolating the all-S isomer, of formula XII.

Compounds of the formula XIV are disclosed, for example, in EP-A 79022 or U.S. Pat. No. 4,587,258.

Besides the abovementioned psychotropic and, in particular, anxiolytic action, the new all-S compounds of the formula III ($R^2$=H or ethyl, $R^3$=n-octyl), and the physiologically tolerated salts thereof, exhibit a strong nootropic action, i.e. improving cognitive function. They are therefore suitable for the treatment of cognitive dysfunctions of various etiologies such as occur, for example, in Alzheimer's disease or senile dementia. The nootropic action of the compounds according to the invention was tested on mice, which had a body weight of 20–25 g, in the inhibitory (passive) avoidance test (step-through model). A modified form of the test method described by J. KOPP, Z. BODA-NECKY and M. E. JARVIK has been described by J. BURES, O. BURESOVA and J. HUSTON in "Techniques and Basic Experiments for the Study of Brain and Behavior", Elsevier Scientific Publishers, Amsterdam (1983).

According to the statements in this literature, a substance is said to have nootropic activity when it is able to abolish the amnesia induced in the experimental animals by an electroconvulsive shock, or the amnesia induced by scopolamine.

The experiments were carried out by modified test methods. The comparison compound used was the known nootropic agent 2-oxo-1-pyrrolidinylacetamide (piracetam). The distinct superiority of the compounds according to the invention over the comparison substance was evident from the fact that it was possible to abolish the scopolamine-induced amnesia in the inhibitory avoidance test with an oral MED (minimal effective dose) of 0.03–30 mg/kg. The comparison substance had an oral MED of about 500–1,000 mg/kg.

Hence the invention also relates to the use of the compounds according to the invention for the treatment and prophylaxis of cognitive dysfunctions.

The invention furthermore embraces pharmaceuticals containing the said new active substances, processes for the preparation thereof, and the use of the compounds according to the invention for the preparation of pharmaceuticals used for the treatment and prophylaxis of the abovementioned pathologies in mammals such as monkeys, dogs, cats, rats, humans etc.

The invention furthermore embraces pharmaceuticals containing the said compounds of the formulae I and II, processes for the preparation thereof, and the use of the compounds according to the invention for the preparation of pharmaceuticals which are used for the treatment and prophylaxis of disorders of the central nervous system, especially of anxiety states.

Applying the method according to the invention, it is possible to use the angiotensin converting enzyme inhibitors of the formulae I and II described above in mammals such as monkeys, dogs, cats, rats, humans etc.

The pharmaceuticals are prepared by processes known per se and familiar to the expert. As pharmaceuticals, the pharmacologically active compounds (=active substance) according to the invention are employed either as such or, preferably, in combination with suitable pharmaceutical auxiliaries in the form of tablets, coated tablets, capsules, suppositories, emulsions, suspensions or solutions, with the content of active substance being up to about 95%, preferably between 10 and 75%.

The auxiliaries suitable for the desired pharmaceutical formulation are familiar to the expert on the basis of his expert knowledge. Besides solvents, gel-formers, suppository bases, tablet auxiliaries and other active substance vehicles it is possible to use, for example, antioxidants, dispersing agents, emulsifiers, antifoam agents, flavorings, preservatives, solubilizers or colorants.

The active substances can be administered, for example, orally, rectally or parenterally (for example intravenously or subcutaneously); with oral administration being preferred.

For a form for oral use, the active compounds are mixed with the additives suitable for this purpose, such as excipients, stabilizers or inert diluents, and converted by customary methods into suitable dosage forms, such as tablets, coated tables, hard gelatin capsules, aqueous, alcoholic or oily suspensions or aqueous, alcoholic or oily solutions. Examples of inert vehicles which can be used are gum arabic, magnesia, magnesium carbonate, lactose, glucose or starch, especially corn starch. This formulation can be carried out both as dry and as wet granules. Examples of suitable oily excipients or solvents are vegetable or animal oils, such as sunflower oil or fish liver oil.

For subcutaneous or intravenous administration, the active compounds, or the physiologically tolerated salts thereof, are converted into a solution, suspension or emulsion, if desired with the substances customary for this purpose, such as solubilizers, emulsifiers or other auxiliaries. Examples of suitable solvents are water, physiological saline or alcohols, for example ethanol, propanol or glycerol, as well as sugar solutions such as glucose or mannitol solutions, or else a mixture of the various solvents mentioned.

The examples which follow are intended to illustrate the compounds and processes according to the invention without confining the invention to the substances and processes mentioned here as representative. Also indicated are forms for use for the prophylaxis and treatment of disorders of the central nervous system by the method according to the invention.

EXAMPLE 1 n-Octyl 2-[N-(1S-ethoxycarbonyl-3-phenylpropyl)-S-alanyl]-(1S,3S,5S)-2-azabicyclo[3.3.0]octane-3-carboxylate 2.07 g (5 mmol) of 2-[N-(1S-ethoxycarbonyl-3-phenylpropyl)-S-alanyl]-(1S,3S,5S)-2-azabicyclo[3.3.0]octane-3-carboxylic acid (ramipril) and 0.50 g (5 mmol) of potassium bicarbonate are stirred in 25 ml of dimethylformamide at 40° C. for 1.5 hours and, after cooling to room temperature, a solution of 1.16 g (6 mmol) of 1-bromooctane in 20 ml of dimethylformamide is added dropwise, and the mixture is stirred at room temperature overnight. The pH is adjusted to 6 by addition of 0.1N HCl, the mixture is diluted with water and extracted three times with methylene chloride, and the combined organic phases are dried, concentrated and purified by column chromatography on 120 g of silica gel (mobile phase toluene/ethanol 98:2). Yield: 2.35 g (89%) of oily product; $[\alpha]_D^{25} = -23.9°$ (c=1, methanol)

EXAMPLE 2

Hydrogen maleate of n-octyl 2-[N-(1S-ethoxycarbonyl-3-phenylpropyl)-S-alanyl]-(1S,3S,5S)-2-azabicyclo[3.3.0]-octane-3-carboxylate 528 mg (1 mmol) of an amine obtained as in Example 1 are dissolved in 20 ml of ether, and a solution of 116 mg (1 mmol) of maleic acid in 4 ml of acetone is added. The solvent is evaporated off, and the residue is crystallized using diisopropyl ether. Yield: 0.51 g (79%) of colorless crystals, melting point 89°–90° C.

EXAMPLE 3 n-Octyl 2-[N-(1S-ethoxycarbonyl-3-phenylpropyl)-S-alanyl]-(1S,3S,5S)-2-azabicyclo[3.3.0]octane-3-carboxylate A solution of 1.31 g (7.5 mmol) of diethyl azodicarboxylate in 10 ml of absolute tetrahydrofuran is added dropwise, at 0° C., to a solution of 1.97 g (7.5 mmol) of triphenylphosphine and 0.65 g (5 mmol) of n-octanol in 100 ml of absolute tetrahydrofuran and, after stirring for 10 minutes, at 0° C. a solution of 2.08 g (5 mmol) of 2-[N- (1S-ethoxycarbonyl-3-phenylpropyl)-S-alanyl]-(1S,3S,5S)-2-azabicyclo[3.3.0]octane-3-carboxylic acid (ramipril) in 25 ml of absolute tetrahydrofuran is added, and the mixture is stirred at 0° C. for 1 hour and at room temperature overnight. The reaction solution is concentrated, the residue is taken up in ethyl acetate, the solution is washed twice with 2N sodium hydroxide solution and once with water, dried and concentrated, and the crude product (5.0 g) is purified by flash chromatography on 200 g of silica gel (mobile phase methylene chloride/ethyl acetate 9:1). 0.83 g (31%) of the title compound is obtained.

EXAMPLE 4 n-Octyl 2-[N-(1S-carboxy-3-phenylpropyl)-S-alanyl]-(1S,3S,5S)-2-azabicyclo[3.3.0]octane-3-carboxylate 2.65 g (5 mmol) of the ethyl ester from Example 1 are dissolved in 18 ml of tetrahydrofuran, 7.5 ml of 1N sodium hydroxide solution are added, and the mixture is stirred at room temperature for 48 hours. It is neutralized by addition of 7.5 ml of 1N hydrochloric acid. The reaction mixture is concentrated, the residue is suspended in water, the suspension is extracted twice with ethyl acetate, the combined organic phases are washed with saturated sodium chloride solution, dried and concentrated, and the crude product (2.05 g) is purified by chromatography on 80 g of silica gel (toluene/ethanol 9:1). The product obtained in this way (1.15 g; 46%) is triturated in 50 ml of petroleum ether, left to stand in the cold, filtered off with suction and dried. Yield: 0.83 g of colorless crystals; melting point 56–61° C.

EXAMPLE 5 n-Octyl 2-[N-(1S-ethoxycarbonyl-3-phenylpropyl)-S-alanyl]-(1S,3S,5S)-2-azabicyclo[3.3.0]octane-3-carboxylate 1.40 g (2.8 mmol) of the carboxylic acid from Example 4 are stirred in 25 ml of ethanolic hydrochloric acid at room temperature for 3 days. The mixture is then concentrated, the residue is taken up in ethyl acetate, the solution is washed three times with saturated sodium bicarbonate solution and once with water, dried and concentrated, and the crude product is purified by column chromatography (mobile phase toluene/ethanol 98:2). 850 mg (57%) of the title compound are obtained.

EXAMPLE 6 n-Octyl 2-[N-(1S-ethoxycarbonyl-3-phenylpropyl)-S-alanyl]-(1S,3S,5S)-2-azabicyclo[3.3.0]octane-3-carboxylate 2.50 g (5 mmol) of the carboxylic acid from Example 4 and 1.00 g (10 mmol) of potassium bicarbonate are stirred in 25 ml of dimethylformamide at 40° C. for 1 hour and, after cooling to room temperature, a solution of 0.66 g (6 mmol) of bromoethane in 20 ml of dimethylformamide is added dropwise, and the mixture is stirred at room temperature overnight. It is poured into water, the mixture is extracted three times with ethyl acetate, the combined organic phases are washed several times with water, dried and concentrated, and the crude product is purified by column chromatography on silica gel (mobile phase toluene/ethanol 98:2). 210 g (80%) of the title compound are obtained.

EXAMPLE 7 n-Octyl 2-[N-(1S-ethoxycarbonyl-3-phenylpropyl)-S-alanyl]-(1S,3S,5S)-2-azabicyclo[3.3.0]octane-3-carboxylate (7a) Benzyl 2-tert.butyloxycarbonyl-(1S,3S,5S)-2-azabicyclo[3.3.0]octane-3-carboxylate A solution of 39.2 g (0.180 mol) of di-tert.-butyl dicarbonate in 60 ml of absolute methylene chloride is slowly added dropwise, at 0° C., to a solution of 40.0 g (0.163 mol) of benzyl (1S,3S,5S)-2-azabicyclo[3.3.0]-octane-3-carboxylate and 23.4 ml (0.169 mol) of absolute triethylamine in 300 ml of absolute methylene chloride, and the mixture is then stirred at 0° C. for 15 minutes and at room temperature for one hour. The reaction solution is washed with 10% strength citric acid solution, saturated sodium bicarbonate solution and water, dried and concentrated. Yield: 55.6 g of oily product $[\alpha]_D^{25} = -1.2°$ (c=2, methanol)

(7b) 2-tert.-Butyloxycarbonyl-(1S,3S,5S)-2-azabicyclo[3.3.0]octane-3-carboxylic acid 55.6 g (0.16 mol) of the benzyl ester from Example 7a) are hydrogenated on 4 g of palladium/charcoal (10%) in 2 liters of ethanol at room temperature for 2.5 hours. The caalyst is filtered off with suction, and the filtrate is concentrated. Yield: 37.3 g (90%) $[\alpha]_D^{25} = +22.7°$ (c=1, methanol)

(7c) n-Octyl 2-tert.-butyloxycarbonyl-(1S,3S,5S)-2-azabicyclo[3.3.0]octane-3-carboxylate 32.3 g (0.127 mol) of the acid from Example 7b) and 25.3 g (0.253 mol) of potassium bicarbonate are stirred in 500 ml of dimethylformamide at 40° C. for 1.5 hours. After cooling, 48.9 g (0.253 mol) of 1-bromooctane are added dropwise, and the mixture is stirred at room temperature overnight. The reaction mixture is poured into water, the mixture is extracted three times with ethyl acetate, the combined organic phases are washed with saturated sodium bicarbonate solution and water, dried and concentrated, and the crude product (44.3 g) is purified by flash chromatography on silica gel (900 g; mobile phase toluene/ethanol 95:5 and 99.5:0.5) in two portions. Yield: 35.4 g (76%) of oily product $[\alpha]_D^{25} = +5.7°$ (c=1, methanol)

(7d) n-Octyl (1S,3S,5S)-2-azabicyclo[3.3.0]octane-3-carboxylate 2.6 g (7.0 mmol) of the BOC compound from Example 7c) are stirred with 9 ml of trifluoroacetic acid at 0° C. for 1.5 hours. The excess acid is removed by evaporation in vacuo, the residue is taken up in water, the mixture is made basic with sodium bicarbonate and is extracted with ethyl acetate, the organic phase is washed once more with water, dried and concentrated, and the product is quickly reacted further. Yield: 1.8 g (95%) of oily product.

(7e) n-Octyl 2-[N-(1S-ethoxycarbonyl-3-phenylpropyl)-S-alanyl]-(1S,3S,5S)-2-azabicyclo[3.3.0]octane-3-carboxylate To a solution of 1.76 g (6.6 mmol) of the amine from Example 7d) in 10 ml of methylene chloride are successively added dropwise, at −10° C., 6.44 g (56 mmol) of N-ethylmorpholine, 1.84 g (6.6 mmol) of N-(1S-ethoxycarbonyl-3-phenylpropyl)-S-alanine and 4 ml of propanephosphonic anhydride (50% in methylene chloride). The mixture is then stirred at 0° C. for 3 hours and at room temperature for 3 hours and is concentrated, the residue is poured into water, the mixture is extracted with ethyl acetate, and the organic phase is washed with water, 25% strength sodium bisulfate solution and saturated sodium bicarbonate solution. The solution is dried, concentrated and purified by column chromatography on silica gel (mobile phase toluene/ethanol 98:2). 2.47 g (71%) of the title compound are obtained.

EXAMPLE 8

Hydrogen maleate of n-octyl 2-[N-(1S-ethoxycarbonyl-3-phenylpropyl)-S-alanyl]-(1S,3S,5S)-2-azabicyclo[3.3.0]-octane-3-carboxylate (8a) Hydrochloride of n-octyl (1S,3S,5S)-2-azabicyclo[3.3.0]octane-3-carboxylate 16.3 g (150 mmol) of distilled trimethylsilyl chloride are added dropwise, at 40° C., to a suspension of 10 g (64 mmol) of (1S,3S,5S)-2-azabicyclo[3.3.0]octane-3-carboxylic acid in 100 ml of distilled n-octanol, and the mixture is stirred at 40° C. overnight. The volatile constituents are removed in a rotary evaporator, the octanol is removed by short-path distillation under high vacuum, the distillation residue is taken up in methylene chloride, the solution is concentrated, and the residue is triturated twice with diisopropyl ether. 14.6 g (75%) of the title compound are obtained. Melting point 76°–78° C. $[\alpha]_D^{25} = -23.7°$ (c=1, methanol)

(8b) Hydrogen maleate of n-octyl 2-[N-(1S-ethoxycarbonyl-3-phenylpropyl)-S-alanyl]-(1S,3S,5S)-2-azabicyclo[3.3.0] octane-3-carboxylate 2.0 g (6.6 mmol) of the amine hydrochloride from Example (8a) are suspended in 30 ml of methylene chloride and 10 ml of water and the pH is adjusted to 9–10 by addition of saturated potassium carbonate solution. Then 1.84 g (6.6 mmol) of N-(1S-ethoxycarbonyl-3-phenylpropyl)-S-alanine and a solution of 4.1 ml of methylethylphosphinic anhydride in 4 ml of methylene chloride are successively added. The mixture is stirred overnight at room temperature and is diluted with methylene chloride and water, the organic phase is washed with a potassium sulfate/potassium bisulfate buffer, sodium bicarbonate solution and sodium chloride solution, dried and concentrated, and the title compound is precipitated from the crude product (2.92 g) by dissolving in 33 ml of diisopropyl ether and adding a solution of 766 mg of maleic acid in 4 ml of acetone. 2.50 g (67%) are obtained.

EXAMPLE 9 n-Octyl 2-[N-(1S-ethoxycarbonyl-3-phenylpropyl)-S-alanyl](1S,3S,5S)-2-azabicyclo[3.3.0]octane-3-carboxylate (9a) n-Octyl 2-[N-tert.butyloxycarbonyl-S-alanyl](1S,3S,5S)-2-azabicyclo[3.3.0]octane-3-carboxylate 10 ml of a solution of propanephosphonic anhydride (50% in methylene chloride) are slowly added dropwise to a mixture of 2.67 g (10 mmol) of the amine from Example 7d), 1.89 g (10 mmol) of BOC-S-alanine and 1.00 g (10 mmol) of triethylamine in 50 ml of absolute dimethylformamide in an ice bath, and the mixture is stirred at room temperature for 4 hours. 200 ml of water are added to the solution, which is then extracted twice with ethyl acetate, the combined organic phases are washed with water, 10% strength citric acid solution, saturated sodium bicarbonate solution and saturated sodium chloride solution, dried and concentrated, and the crude product is purified by column chromatography on silica gel (mobile phase toluene/ethanol 99:1). 3.05 g (70%) of the title compound are obtained. $[\alpha]_D^{25} = -39.9°$ (c=1, methanol)

(9b) n-Octyl 2-(S-alanyl)-(1S,3S,5S)-2-azabicyclo[3.3.0]-octane-3-carboxylate 6.70 g (15.9 mmol) of the BOC compound from Example 9a) are stirred in 30 ml of trifluoroacetic acid at 0° C. for 90 minutes. The solvent is evaporated off, the residue is taken up in ethanol, and the mixture is neutralized by addition of potassium carbonate, filtered and concentrated. 5.3 g (98%) of the title compound are obtained.

(9c) n-Octyl 2-[N-(1S-ethoxycarbonyl-3-phenylpropyl-S-alanyl]-(1S,3S,5S)-2-azabicyclo[3.3.0]octane-3-carboxylate To a solution of 1.35 g (4.0 mmol) of the amine from Example 9b) in 25 ml of absolute methylene chloride are successively added, at 0° C., 0.8 g (8 mmol) of triethylamine and a solution of 1.36 g (4 mmol) of ethyl 4-phenyl-(2R)-trifluoromethylsulfonyloxybutyrate in 10 ml of absolute methylene chloride, and the mixture is stirred at room temperature overnight. The reaction solution is washed with water, dried and concentrated, and the crude product is purified by column chromatography on silica gel (mobile phase toluene/ethanol 99.5:0.5, 99:1). 0.28 g (13%) of the title compound is obtained.

EXAMPLE 10

Preparation of the agent employed according to the invention for oral use in the treatment and prophylaxis of cognitive dysfunctions, and for the treatment and prophylaxis of disturbances of the central nervous system.

1,000 tablets each containing 10 mg of n-octyl 2-[N-(1-S-carbethoxy-3-phenyl-propyl)-S-alanyl]-1S,3S,5S-2-azabicyclo[3.3.0]octane-3-carboxylate are prepared using the following auxiliaries:

| | |
|---|---|
| n-Octyl 2-[N-(1-S-carbethoxy-3-phenyl-propyl)-s-alanyl]-(1S,3S,5S)-2-azabicyclo[3.3.0]octane-3-carboxylate | 10 g |
| Corn starch | 140 g |
| Gelatin | 7.5 g |
| Microcrystalline cellulose | 2.5 g |
| Magnesium stearate | 2.5 g | n-Octyl 2-[N-(1-S-carbethoxy-3-phenyl-propyl)-S-alanyl](1S,3S,5S)-2-azabicyclo[3.3.0]octane-3-carboxylate and corn starch are mixed with an aqueous gelatin solution. The mixture is dried and converted into granules by milling. Microcrystalline cellulose and magnesium stearate are mixed with the granules. The resulting granules are compressed to form 1,000 tablets, each tablet containing 10 mg of the active substance. These tablets can be used for the abovementioned indications.

EXAMPLE 11

In analogy to Example 10, 1,000 tablets each containing 10 mg of 1'-[N-(1-S-carbethoxy-3-phenylpropyl)-S-alanyl](3'S,5'S)-spirobicyclo[2.2.2]octane-2,3'-pyrrolidine-5'-carboxylic acid are prepared.

EXAMPLE 12

Gelatin capsules each containing 10 mg of 1'-[N-(1-S-carbethoxy-3-phenylpropyl)-S-alanyl]-(3'S,5'S)-spirobicyclo[2.2.2]octane-2,3'-pyrrolidine-5'-carboxylic acid are filled with the following mixture:

| | |
|---|---|
| 1'-[N-(1-S-carbethoxy-3-phenylpropyl)-S-alanyl]-(3'S,5'S)-spirobicyclo[2.2.2]octane-2,3'-pyrrolidine-5'-carboxylic acid | 10 mg |
| Magnesium stearate | 1 mg |
| Lactose | 214 mg |

These capsules can be used for the treatment and prophylaxis of disorders of the central nervous system.

EXAMPLE 13

The preparation of an injectable solution is described below:

| | |
|---|---|
| 2-[N-(1-S-Carboxy-3-phenyl-propyl)-S-alanyl]-(1S,3S,5S)-2-azabicyclo[3.3.0]octane-3-carboxylic acid | 250 mg |
| Methylparaben | 5 g |
| Propylparaben | 1 g |
| Sodium chloride | 25 g |
| Water for injections | 5 l |

2-[N-(1-S—Carboxy-3-phenyl-propyl)-S-alanyl]-(1S,3S,5S)-2-azabicyclo[3.3.0]octane-3-carboxylic acid, the preservatives and sodium chloride are dissolved in 3 l of water for injections and made up to 5 l with water for injections. The solution is filtered sterile and dispensed aseptically into previously sterilized bottles, which are closed with sterilized rubber caps. Each bottle contains 5 ml of solution.

EXAMPLE 14

Tablets which can be u$ed for the treatment or prophylaxis of disorders of the central nervous system are prepared as described in Example 10, with the exception that 2-[N-(1-S-carboxy-3-phenyl-propyl)-S-alanyl]-(1S,3S,5S)-2azabicyclo[3.3.0]octane-3-carboxylic acid or 1-[N-(1-S-carboxy-3-phenyl-propyl)-S-alanyl]-(2S,3aR,7aS)-octahy-droindole-2-carboxylic acid or 1-[N-(1-S-carbethoxy-3-phenyl-propyl)-S-alanyl]-cis-2,3,3a,4,5,7a-hexahydro[1H]-indol-2-S-endo-carboxylic acid or 1-[N-(1-S-carboxy-3-phenyl-propyl)-S-alanyl]-cis-2,3,3a,4,5,7a-hexahydro[1H]in-dole-2S-endo-carboxylic acid or 2-[N-(1-S-carboxy-3-phenyl-propyl)-S-lysyl]-(1S,3S,5S)-2-azabicyclo[3.3.0]octane-3-carboxylic acid or 2-[N-(1-S-carbethoxy-3-cyclohexyl-propyl)-S-alanyl]-(1S,3S,5S)-2-azabicyclo[3.3.0]octane-3-carboxylic acid or N-(1-S-carboxy-3-cyclohexyl-propyl)-S-lysyl(1S,3S,5S)-2-azabicyclo[3.3.0]octane-3-carboxylic acid or 1'-[N-(1-S-carbethoxy-3-phenyl-propyl)-S-alanyl]-exo-spiro-bicyclo[2.2.2]octane-2,3'-pyrrolidine-5'-S-carboxylic acid or (S,S,S)-1-methyl-2-(1-carbethoxy-3-phenyl-propyl)-2H-undecahydro-cyclopenta[4.5]pyrrolo[1,2-a]pyrazine-3,8-dione or 1'-[N-(1-S-carbethoxy-3-phenylpropyl)-S-alanyl]-endo-spiro-bicyclo[2.2.2]octane-2,3'-pyrrolidinyl-5'-S-carboxylic acid or n-octyl 2-[N-(1-S-carbethoxy-3-phenylpropyl)-S-alanyl]-cis-endo-2-azabicyclo[3.3.0]octane-3-S-carboxylate or decyl 2-[N-(1-S-carbethoxy-3-phenylpropyl)-S-alanyl]-cis-endo-2-azabicyclo[3.3.0]octane-3-S-carboxylate or 5-nonyl 2-[N-(1-S-carbethoxy-3-phenylpropyl)-S-alanyl]-cis-endo-2-azabicyclo[3.3.0]octane-3-S-carboxylate or n-octyl 2-[N-(1-S-octyloxy-3-phenylpropyl)-S-alanyl]-cis-endo-2-azabicyclo[3.3.0]octane-3-S-carboxylate or benzhydryl 2-[N-(1-S-menthyloxy-3-phenylpropyl)-S-alanyl]-cis-endo-2-azabicyclo[3.3.0]octane-3-S-carboxylate are used in place of n-octyl 2-[N-(1-S-carbethoxy-3-phenyl-propyl)-S-alanyl]-(1S,3S,5S)-2-azabicyclo[3.3.0]octane-3S-carboxylate.

EXAMPLE 15

An injectable solution is prepared in analogy to the procedure described in Example 13, with the exception that 2-[N-(1-S-carboxy-3-phenyl-propyl)-S-alanyl]-(1S,3S,5S)-2-azabicyclo[3.3.0]octane-3-carboxylic acid or 1-[N-(1-S-carbethoxy-3-phenyl-propyl)-S-alanyl]-(2S,3aR,7aS)-octahydroindole-2-carboxylic acid hydrochloride or 1-[N-(1-S-carboxy-3-phenyl-propyl)-S-alanyl]-(2S,3aR,7aS)-octahydroindole-2-carboxylic acid or 1-[N-(1-S-carbethoxy-3-cyclohexyl-propyl)-S-alanyl]-cis-2,3,3a,4,5,7a-hexahydro[1H]indole-2-S-endo-carboxylic acid or 1-[N-(1-S-carboxy3-phenyl-propyl)-S-alanyl]-cis-2,3,3a,4,5,7a-hexahydro[1H]indole-2-S-endo-carboxylic acid or 2-[N-(1-carboxy-3-phenyl-propyl)-S-lysyl]-(1S,3S,5S)-2-azabicyclo[3.3.0]octane-3carboxylic acid or 2-[N-(1-S-carbethoxy-3-cyclohexyl-propyl)-S-alanyl]-(1S,3S,5S)-2-azabicyclo[3.3.0]octane-3-carboxylic acid or 2-[N-(1-S-carboxy-3-cyclohexyl-propyl)-S-lysyl](1S,3S,5S)-2-azabicyclo[3.3.0]octane-3-carboxylic acid or 1'[N-(1-S-carboxy-3-phenylpropyl)-S-alanyl]-endo-spirobicyclo[2.2.2]octane-2,3'-pyrrolidine-5'-S-carboxylic acid or 1'[N-(1-S-carboxy-3-phenylpropyl)-S-alanyl]-exo-spirobicyclo[2.2.2]octane-2,3'-pyrrolidine-5'-S-carboxylic acid are used in place of 2-[N-(1-S-carbethoxy-3-phenyl-propyl)-S-alanyl]-(1S,3S,5S)-2-azabicyclo[3.3.0]octane-3-carboxylic acid.

Example 16

Preparation of the agent employed according to the invention for oral use in the treatment and prophylaxis of cognitive dysfunctions, and for the treatment and prophylaxis of disorders of the central nervous system.

1,000 tablets each containing 15 mg of the maleate of n-octyl 2-[N-(1-S-carbethoxy-3-phenyl-propyl)-S-alanyl]1S,3S,5S-2-azabicyclo[3.3.0]octane-3-carboxylate are prepared using the following auxiliaries:

| | |
|---|---|
| maleate of n-octyl 2-[N-(1S-carbethoxy-3-phenyl-propyl)-S-alanyl]-(1S,3S,5S)-2-azabicyclo[3.3.0]octane-3-carboxylate | 15 g |
| corn starch | 200 g |
| gelatin | 10 g |
| microcrystalline cellulose | 4 g |
| magnesium stearate | 4 g |

The maleate of n-octyl 2-[N-(1-S-carbethoxy-3-phenyl-propyl)-S-alanyl]-(1S,3S,5S)-2-azabicyclo[3.3.0]octane-3-carboxylate and corn starch are mixed with an aqueous gelatin solution. The mixture is dried and converted into granules by milling. Microcrystalline cellulose and magnesium stearate are mixed with the granules. The resulting granules are compressed to form 1,000 tablets, each tablet containing 15 mg of the active substance. These tablets can be used for the abovementioned indications.

Example 17

Preparation of the agent employed according to the invention for oral use in the treatment and prophylaxis of cognitive dysfunctions, and for the treatment and prophylaxis of disorders of the central nervous system. 1,000 tablets each containing 8 mg of n-octyl 2-[N-(1-S-carboxy-3-phenyl-propyl)-S-alanyl]-1S,3S,5S-2-azabicyclo[3.3.0]octane-3-carboxylate are prepared using the following auxiliaries:

| n-octyl 2-[N-(1S-carboxy-3-phenyl-propyl)-S-alanyl]-(1S,3S,5S)-2-azabicyclo-[3.3.0]octane-3-carboxylate | 8 g |
|---|---|
| corn starch | 120 g |
| gelatin | 7 g |
| microcrystalline cellulose | 2 g |
| magnesium stearate | 2 g | n-Octyl 2-[N-(1-S-carboxy-3-phenyl-propyl)-S-alanyl]-(1S,3S,5S)-2-azabicyclo[3.3.0]octane-3-carboxylate and corn starch are mixed with an aqueous gelatin solution. The mixture is dried and converted into granules by milling. Microcrystalline cellulose and magnesium stearate are mixed with the granules. The resulting granules are compressed to form 1,000 tablets, each tablet containing 8 mg of the active substance. These tablets can be used for the abovementioned indications.

We claim:

1. A compound of the formula III

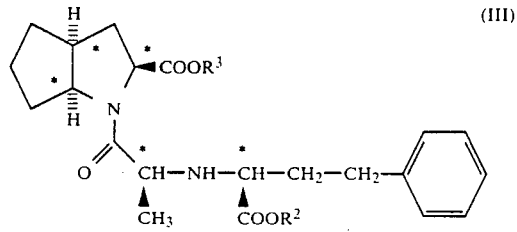

in which the five chiral carbon atoms (*) each have the S configuration,
   $R^2$ denotes ethyl or hydrogen, and
   $R^3$ denotes n-octyl, or a physiologically tolerated salt thereof.

2. A compound of the formula III as claimed in claim 1, in which $R^2$ denotes ethyl, or a physiologically tolerated salt thereof.

3. A compound of the formula III as claimed in claim 1, in which $R^2$ denotes hydrogen, or a physiologically tolerated salt thereof.

4. The maleate of the compound as claimed in claim 2.

5. A method for the treatment of at least one cognitive dysfunction, which comprises the step of administering a nootrophically effective amount of a compound as claimed in claim 1, or a physiologically tolerated salt thereof.

6. A pharmaceutical agent comprising a nootropically effective amount of a compound as claimed in claim 1, or the physiologically tolerated salt thereof, and a physiologically tolerated vehicle.

* * * * *